US009150832B2

(12) United States Patent
KenKnight et al.

(10) Patent No.: US 9,150,832 B2
(45) Date of Patent: Oct. 6, 2015

(54) CELL TRAINING FOR LOCAL FIELD STIMULATION

(75) Inventors: Bruce KenKnight, Maple Grove, MN (US); Steven D. Girouard, Chagrin Falls, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1536 days.

(21) Appl. No.: 11/745,620

(22) Filed: May 8, 2007

(65) Prior Publication Data

US 2008/0280339 A1 Nov. 13, 2008

(51) Int. Cl.
| | |
|---|---|
| C12N 13/00 | (2006.01) |
| A61N 1/362 | (2006.01) |
| C12N 5/077 | (2010.01) |
| A61K 35/12 | (2015.01) |
| A61M 37/00 | (2006.01) |
| A61B 17/34 | (2006.01) |
| A61B 17/00 | (2006.01) |
| A61B 18/00 | (2006.01) |
| A61N 1/32 | (2006.01) |

(52) U.S. Cl.
CPC .............. *C12N 5/0657* (2013.01); *A61K 35/12* (2013.01); *A61M 37/0069* (2013.01); *A61N 1/362* (2013.01); *A61B 17/3468* (2013.01); *A61B 2017/00247* (2013.01); *A61B 2017/00256* (2013.01); *A61B 2018/00392* (2013.01); *A61N 1/326* (2013.01)

(58) Field of Classification Search
CPC .................... A61K 2039/505; C12N 2510/00; C12N 5/0657; A61N 1/05; A61N 5/0601; A01K 2267/0375
See application file for complete search history.

(56) References Cited

U.S. PATENT DOCUMENTS

| | | | |
|---|---|---|---|
| 4,552,150 | A | 11/1985 | Zacouto |
| 6,810,286 | B2 * | 10/2004 | Donovan et al. .................. 607/2 |
| 7,006,871 | B1 | 2/2006 | Darvish et al. |
| 2002/0077687 | A1 | 6/2002 | Ahn |
| 2003/0040777 | A1 | 2/2003 | Shemer et al. |
| 2004/0029148 | A1 | 2/2004 | Feld et al. |
| 2004/0137621 | A1 | 7/2004 | Rosen et al. |
| 2004/0158289 | A1 | 8/2004 | Girouard et al. |
| 2004/0158290 | A1 | 8/2004 | Girouard et al. |
| 2004/0214182 | A1 | 10/2004 | Sharma et al. |
| 2004/0215251 | A1 | 10/2004 | Sharma et al. |
| 2004/0254134 | A1 | 12/2004 | Marban et al. |
| 2005/0021089 | A1 | 1/2005 | Sharma |
| 2005/0021091 | A1 | 1/2005 | Laske et al. |
| 2005/0037489 | A1 | 2/2005 | Gepstein et al. |
| 2005/0054092 | A1 | 3/2005 | Xu et al. |
| 2005/0192637 | A1 | 9/2005 | Girouard et al. |
| 2005/0288721 | A1 | 12/2005 | Girouard et al. |
| 2006/0015146 | A1 | 1/2006 | Girouard et al. |
| 2006/0149184 | A1 | 7/2006 | Soykan et al. |
| 2007/0027487 | A1 | 2/2007 | Mika et al. |
| 2007/0053886 | A1 * | 3/2007 | Rosen et al. .................. 424/93.7 |
| 2009/0053180 | A1 * | 2/2009 | Rosen et al. .................. 424/93.7 |

FOREIGN PATENT DOCUMENTS

| | | |
|---|---|---|
| WO | WO 00/69504 A1 | 11/2000 |
| WO | WO 02/098286 A2 | 12/2002 |
| WO | WO 2007/014134 A2 | 2/2007 |
| WO | WO 2007/030834 A1 | 3/2007 |

OTHER PUBLICATIONS

Qu et al., 2003, Circulation, 107: 1106-1109.*
Tang et al., 2004, Regulatory Peptides, 117: 3-10.*
Murphy et al., 2001, Anesthesiology, 95:A685.*
Definition of sub-threshold. Retrieved from: http://www.physiologyweb.com/glossary/s/sub_threshold.html on Jun. 20, 2015.*
Akar, Fadi G. et al. "Optical Measurement of Cell-to-Cell Coupling in Intact Heart Using Subthreshold Electrical Stimulation" *Am. J. Physiol. Heart Circ. Physiol.* 281:H533-H542 (2001).
Altomare, Claudia et al. "Integrated Allosteric Model of Voltage Gating of HCN Channels" *J. Gen. Physiol.* 117:519-532 (2001).
Biel, Martin et al. "Cardiac HCN Channels: Structure, Function, and Modulation" *Trends Cardiovasc. Med.* 12:206-213 (2002).
Bucchi, Annalisa et al. "Wild-type and Mutant HCN Channels in a Tandem Biological-Electronic Cardiac Pacemaker" *Circulation* 114:992-999 (2006).
Chen, Jun et al. "The S4-S5 Linker Couples Voltage Sensing and Activation of Pacemaker Channels" *PNAS* 98(20):11277-11282 (2001).

(Continued)

*Primary Examiner* — Thaian N Ton
*Assistant Examiner* — Titilayo Moloye

(57) ABSTRACT

A system is provided for stimulating one or more cells, wherein the stimulation is sub-threshold and may alter a transmembrane potential of the one or more cells. For some populations of cells it may be possible to affect the transmembrane potential to gain a therapeutic benefit. Cells of the sino-atrial node spontaneously depolarize predominantly due to the slow depolarization of transmembrane potential. The present system may provide sino-atrial cells with a local field stimulation that while not eliciting an action potential may nonetheless alter local transmembrane potential. Such alteration of transmembrane potential may permit an increase or decrease in a rate of depolarization, and hence modify heart rate.

7 Claims, 9 Drawing Sheets

(56) References Cited

OTHER PUBLICATIONS

Cho, Hee Cheol et al. "Creation of a Biological Pacemaker by Cell Fusion" *Circulation* 112(17 Suppl.):II-307, Abstr. 1544 (2005).
Cho, Hee Cheol et al. "Conversion of Non-Excitable Cells to Self-Contained Biological Pacemakers" *Circulation* 112(17 Suppl.):II-307, Abstr. 1545 (2005).
Cohen, Ira S. et al. "The Why, What, How and When of Biological Pacemakers" *Nat. Clin. Pract. Cardiovasc. Med.* 2(8):374-375 (2005).
Cowan, Douglas B. et al. "A Paradigm Shift in Cardiac Pacing Therapy?" *Circulation* 114:986-988 (2006).
Edelberg, Jay M. et al. "Enhancement of Murine Cardiac Chronotropy by the Molecular Transfer of the Human $\beta_2$ Adrenergic Receptor cDNA" *J. Clin. Invest.* 101(2):337-343 (1998).
Edelberg, J. M. et al. "Molecular Enhancement of Porcine Cardiac Chronotropy" *Heart* 86:559-562 (2001).
Fishler, Matthew G. et al. "Mechanisms of Cardiac Cell Excitation with Premature Monophasic and Biphasic Field Stimuli: a Model Study" *Biophysical Journal* 70:1347-1362 (1996).
Feld, Yair et al. "Electrophysiological Modulation of Cardiomyocytic Tissue by Transfected Fibroblasts Expressing Potassium Channels: a Novel Strategy to Manipulate Excitability" *Circulation* 105:522-529 (2002).
Fromherz, Peter et al. "Silicon-Neuron Junction: Capacitive Stimulation of an Individual Neuron on a Silicon Chip" *Physical Review Letters* 75(8):1670-73 (1995).
Gepstein, Lior et al. "Somatic Gene and Cell Therapy Strategies for the Treatment of Cardiac Arrhythmias" *Am. J. Physiol. Heart Circ. Physiol.* 286:H815-H822 (2004).
Kehat, I. et al. "Electromechanical Integration of Cardiomyocytes Derived from Human Embryonic Stem Cells" *Nature Biotechnology* 22(10):1282-1289 (2004).
Knisley, Stephen B. et al. "Virtual Electrode Effects in Myocardial Fibers" *Biophysical Journal* 66:719-728 (1994).
Miake, Junichiro et al. "Biological Pacemaker Created by Gene Transfer" *Nature* 419:132-133 (2002).
Miake, Junichiro et al. "Functional Role of Inward Rectifier Current in Heart Probed by Kir2.1 Overexpression and Dominant-Negative Suppression" *J. Clin. Invest.* 111(10):1529-1536 (2003).
Plotnikov, Alexei N. et al. "Biological Pacemaker Implanted in Canine Left Bundle Branch Provides Ventricular Escape Rhythms that Have Physiologically Acceptable Rates" *Circulation* 109:506-512 (2004).
Potapova, I. et al. "Human Mesenchymal Stem Cells as a Gene Delivery System to Create Cardiac Pacemakers" *Circulation Research* 94:952-959 (2004).
Qu, Jihong et al. "Expression and Function of a Biological Pacemaker in Canine Heart" *Circulation* 107:1106-1109 (2003).
Qu, Jihong et al. "HCN2 Overexpression in Newborn and Adult Ventricular Myocytes-Distinct Effects on Gating and Excitability" *Circulation Research* 89:e8-e14 (2001).
Rosen, Michael R. et al. "Genes, Stem Cells and Biological Pacemakers" *Cardiovascular Research* 64:12-23 (2004).
Rosen, Michael R. "Biological Pacemaking: In Our Lifetime?" *Heart Rhythm* 2(4):418-428 (2005).
Sambelashvili, Aleksandre T. et al. "Nonlinear Effects in Subthreshold Virtual Electrode Polarization" *Am. J. Physiol. Heart Circ. Physiol.* 284:H2368-H2374 (2003).
Satoh, Hiroyasu "Sino-Atrial Nodal Cells of Mammalian Hearts: Ionic Currents and Gene Expression of Pacemaker Ionic Channels" *J. Smooth Muscle Res.* 39(5):175-193 (2003).
Schram, Gernot et al. "Differential Distribution of Cardiac Ion Channel Expression as a Basis for Regional Specialization in Electrical Function" *Circulation Research* 90:939-950 (2002).
Sharma, Vinod et al. "Spatial Heterogeneity of Transmembrane Potential Responses of Single Guinea-Pig Cardiac Cells During Electric Field Stimulation" *Journal of Physiology* 542.2:477-492 (2002).
Sharma, Vinod et al. "Paradoxical Loss of Excitation with High Intensity Pulses During Electric Field Stimulation of Single Cardiac Cells" *Biophysical Journal* 88:3038-3049 (2005).
Tse, Hung-Fat et al. "Bioartificial Sinus Node Constructed via In Vivo Gene Transfer of an Engineered Pacemaker HCN Channel Reduces the Dependence on Electronic Pacemaker in a Sick-Sinus Syndrome Model" *Circulation* 114:1000-1011 (2006).
Choi et al., "Cardiac Conduction Through Engineered Tissue" *American Journal of Pathology*, vol. 169, No. 1, Jul. 2006.
International Search Report and Written Opinion for International Application No. PCT/US2008/058144 mailed Dec. 22, 2008.
International Search Report and Written Opinion of the International Searching Authority for International Application No. PCT/US2008/058259 mailed Apr. 7, 2008.

\* cited by examiner

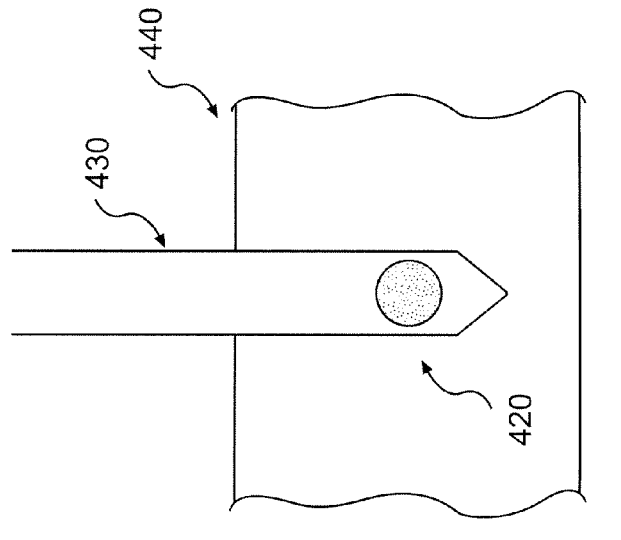
FIG. 6D
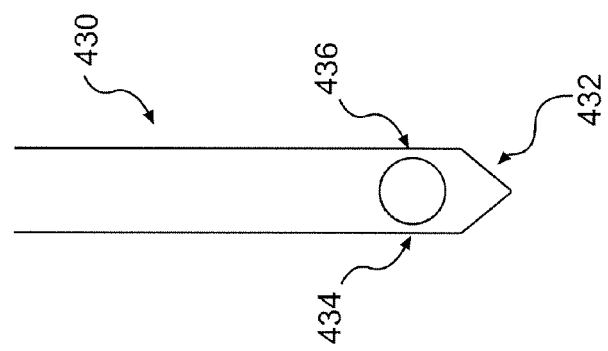
FIG. 6C
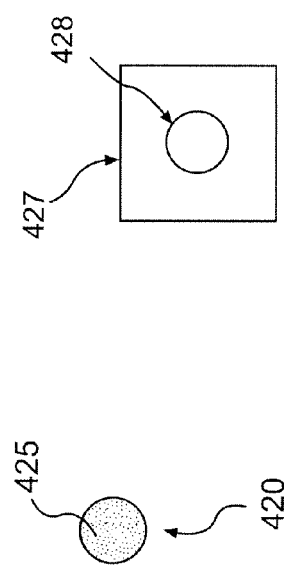
FIG. 6B
FIG. 6A

CELL TRAINING FOR LOCAL FIELD STIMULATION

JOINT RESEARCH AGREEMENT

The present disclosure was made by or on behalf of the below listed parties to a joint research agreement. The joint research agreement was in effect on or before the date the present disclosure was made and the present disclosure was made as a result of activities undertaken within the scope of the joint research agreement. The parties to the joint research agreement are: 1.) Cardiac Pacemakers, Inc., 2.) The Trustees of Columbia University in the City of New York, and 3.) The Research Foundation of the State University of New York.

FIELD OF THE INVENTION

The present invention relates to systems, devices and methods for providing local field stimulation to cells, and more specifically, providing a local field stimulation to treat a cardiac disorder.

BACKGROUND OF THE INVENTION

The heart is an innervated multi-chambered muscular organ that maintains blood flow through the circulatory system of the body. In a normal, healthy heart, blood flow is regulated by a coordinated contraction and relaxation of various heart chambers. The coordinated contraction and relaxation is controlled by periodic electrical depolarizations originating from the sino-atrial (SA) node located in the posterior wall of the right atrium. The SA node is a population of specialized cardiac cells that act as a pacemaker by generating cellular depolarizations, termed action potentials, at regular intervals in response to physiological inputs. The SA node is richly innervated by vagal and sympathetic fibers, making it susceptible to autonomic influences. Stimulation of the vagus nerve for instance causes a decrease in the rate of action potentials generated by the SA node, causing a decrease in heart rate. Conversely stimulation via sympathetic fibers causes an increase in the rate of action potential generation, thereby increasing heart rate and blood flow. Action potentials generated by the SA node are conducted throughout the heart in a regulated manner to ensure coordinated contraction and relaxation of the various chambers.

Coordinated depolarization of cardiac tissue should occur in a controlled manner throughout the heart chambers to maintain high pumping efficiency. A depolarization generated by the SA node is initially conducted through the atria, causing the atria to contract and forcing blood from the atria into the ventricles. The depolarization pulse then conducts to the atrio-ventricular (AV) node and onto a group of specialized conducting myocardial cells termed Purkinje fibers, where it is transmitted through the inter-ventricular septum and ventricles. The depolarized left and right ventricles contract, forcing blood out of the heart and through the circulatory system of the body.

Numerous cardiac pathologies may affect the myocardial depolarization process. For example, acute myocardial events, such as a myocardial infarction, may damage cardiac conduction pathways, leading to altered depolarization progression throughout the myocardium that may decrease cardiac output and/or pumping efficiency. Chronic conditions, such as high blood pressure, valvular disease, certain types of infection, and diabetes may give rise to slowly-progressing conduction disturbances and contraction inefficiencies.

Under some circumstances pharmaceutical therapies may partially restore heart function. Many pharmacologic treatments are effective at increasing cardiac output, preventing arrhythmias, and/or treating symptoms associated with heart failure. However, for some patients, pharmaceutical therapy may be ineffective or inadequate. For example, many patients who have suffered acute or chronic damage to myocardial conduction pathways have lasting and/or recurring arrhythmias. In some patients, conduction through the ventricles may be abnormal and/or the depolarizations may be asynchronous, whereby contractions of the atria and ventricles are poorly coordinated. These condition disturbances may have a deleterious effect on cardiac output, may contribute to the progression of cardiac disease, and may ultimately lead to death.

For some patients implantable cardiac rhythm management (CRM) systems may be used to reduce the effects of conduction abnormalities. CRM systems may include pacemakers and/or defibrillators configured to provide electrical stimulation to specific regions of the myocardium. Pacemakers generally include a pulse generator which houses various electrical components, such as a battery, control hardware, communications systems, and/or other diagnostic components. The pacemaker may also include a number of leads and electrodes configured to transmit an electrical stimulation pulse from the pulse generator to specific regions of the myocardium. Numerous different pacemakers, defibrillators, leads and electrodes are available, depending on the pathology to be treated and clinical factors of the patient.

More recently, various biological therapeutics have been proposed to treat various cardiac pathologies, and some are currently undergoing clinical development. These biological therapies include gene-based and cell-based therapies; gene-based therapies aim to modify or supplement endogenous gene expression of existing cardiomyocytes while cell-based therapies includes augmentation or replacement of existing cardiomyocytes with other cells. It is also possible to combine gene-based and cell-based therapies to genetically modify cells prior to transplantation into the heart. Such therapies may also benefit from advances being developed for stem cell therapeutics.

The various molecular mechanisms underlying cardiac functionality are complex. Numerous ion channels are known to regulate specific ion fluxes across the cellular membranes of cardiomyocytes, and various gap junctions have been identified and shown to allow current flow between adjacent cells. Different distributions of various membrane associated proteins and protein complexes are also thought to contribute to various conduction processes within the myocardium. Recent work has also highlighted the heterogeneity of various myocardial cell populations, revealing molecular differences between cells of the SA node, AV node, Purkinje fibers, atrial myocytes, and ventricular myocytes. Such molecular heterogeneity partially contributes to different electrophysiological activity of the various cardiac cell types, and action potential propagation throughout the myocardium.

Improved molecular and cellular techniques may permit formation of cell types with molecular properties that mimic the cellular functions of the various cell populations of the native heart. For example, cells may be genetically altered to upregulate expression of HCN2 and/or HCN4, ion channels associated with a current (termed "funny" current, $I_f$) that flows across a cell membrane and leads to the spontaneous depolarization of SA node type cells. Genetically altered cells may be engineered to replace or augment the function of natural cardiac pacemaker cells, such as the SA and AV nodes, and upon implantation may help to restore appropriate generation and/or propagation of action potentials.

The spontaneous rate of depolarization of cardiac cells is dependent on the type and density of various ion channels, local ion concentrations, neurohormonal state and the local transmembrane potential. The kinetics of specific types of ion channels may be dependent upon specific current-voltage relationships as transmembrane potential may influence channel gating. Channels of different sequence and/or conformation may exhibit different current-voltage relationships, and different types of channels may activate, deactivate, and/or maintain a particular state at different potentials. Such regulation of channel gating affects the timing and duration of ion fluxes caused by specific ion channels. In the case of the funny current, altering a cell's transmembrane potential through application of a local field can modify the cell's channel kinetics to alter the cell's rate of spontaneous depolarization.

Effective functioning of cells introduced into the myocardium may benefit from concurrent use of a Cardiac Rhythm Management (CRM) system. For example, the introduced pacemaker cells may initially have a limited pacing rate that may be insufficient during high metabolic demand. The introduced cells may also require a training period whereby the CRM system may pace the introduced cells at specific rates to enhance formation of gap functions and/or other proteins required for adequate engraftment. Further, the introduced cells may be temporarily or permanently affected by medications or other condition that may affect normal myocardial cells (e.g. infarction). In addition, a CRM system may be desired to monitor, record, and/or transmit information related to patient status to healthcare professionals to facilitate continued treatment.

The present disclosure provides systems, devices and methods for providing local field stimulation to affect the transmembrane potential of one or more cells.

SUMMARY OF THE INVENTION

For some populations of cells it may be possible to affect the transmembrane potential to gain a therapeutic benefit. For example, cells may be engineered to express HCN2 and/or HCN4, as described above. Spontaneous depolarizations of SA nodal cells are triggered in part by the slow depolarization of transmembrane potential caused by a flow of funny current ($I_f$). A system may provide cells with a local field stimulation (LFS) that while not eliciting an action potential may nonetheless alter local transmembrane potential. Such alteration of transmembrane potential may permit an increase or decrease in a rate of depolarization and hence action potential firing. Such a system may permit provide an effective pacing therapy independent of the specific cell type.

A first aspect of the present invention includes a method of stimulating a cell colony. The method includes applying a local field stimulation (LFS) to a cell colony, wherein the LFS is sub-threshold and alters a transmembrane potential of a cell of the cell colony.

A second aspect of the present invention includes a method of preparing a cell colony for an application of a LFS. The method includes selecting at least one cell capable of forming a cell colony, and forming the cell colony in a cell cassette, wherein the cell cassette is configured to permit application of a LFS to the cell colony to alter a transmembrane potential of a cell of the cell colony.

A third aspect of the present invention includes a method of implanting a cell colony to permit application of a LFS. The method includes placing a cell colony in an insertion device configured to insert the cell colony in a tissue, and implanting the cell colony in the tissue using the insertion device such that application of a LFS will alter a transmembrane potential of a cell of the cell colony.

A forth aspect of the present invention includes a method of extracting a stimulation device. The method includes attaching an extraction device to a stimulation device configured to deliver a LFS to a cell colony located in a tissue and extracting the stimulation device from the tissue.

A fifth aspect of the present invention includes a stimulation device. The stimulation device includes an electrode configured to apply a LFS to a cell colony, wherein the LFS is sub-threshold and alters a transmembrane potential of a cell of the cell colony.

A sixth aspect of the present invention includes a cell cassette. The cell cassette includes a medium configured to receive a cell colony prior to implantation of the cell colony in a tissue. The cell cassette is further configured to permit application of a LFS to the cell colony following implantation of the cell colony, wherein the LFS is sub-threshold and alters a transmembrane potential of a cell of the cell colony.

A seventh aspect of the present invention includes an insertion device. The insertion device includes a device configured to receive and implant a cell cassette in a tissue, wherein the cell cassette is configured to permit application of a LFS to the cell colony to alter a transmembrane potential of a cell of the cell colony.

An eighth aspect of the present invention includes a LFS system. The LFS system includes an energy source configured to transmit an energy signal and a microprocessor operably connected to the energy source and configured to modulate the energy signal. The LFS system also includes an electrode operably connected to the energy source and configured to apply a LFS to a cell colony, wherein the LFS is sub-threshold and alters a transmembrane potential of a cell of the cell colony.

Additional aspects and advantages of the invention will be set forth in part in the description which follows, and in part will be apparent from the description, or can be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 6A illustrates a cell cassette, according to an exemplary disclosed embodiment.

FIG. 6B illustrates a pre-implantation system, according to an exemplary disclosed embodiment.

FIG. 6C illustrates a lead, according to an exemplary disclosed embodiment.

FIG. 6D illustrates a lead and a cell cassette implanted in a target tissue, according to an exemplary disclosed embodiment.

DETAILED DESCRIPTION

Native Cardiac Function

Figure 1:
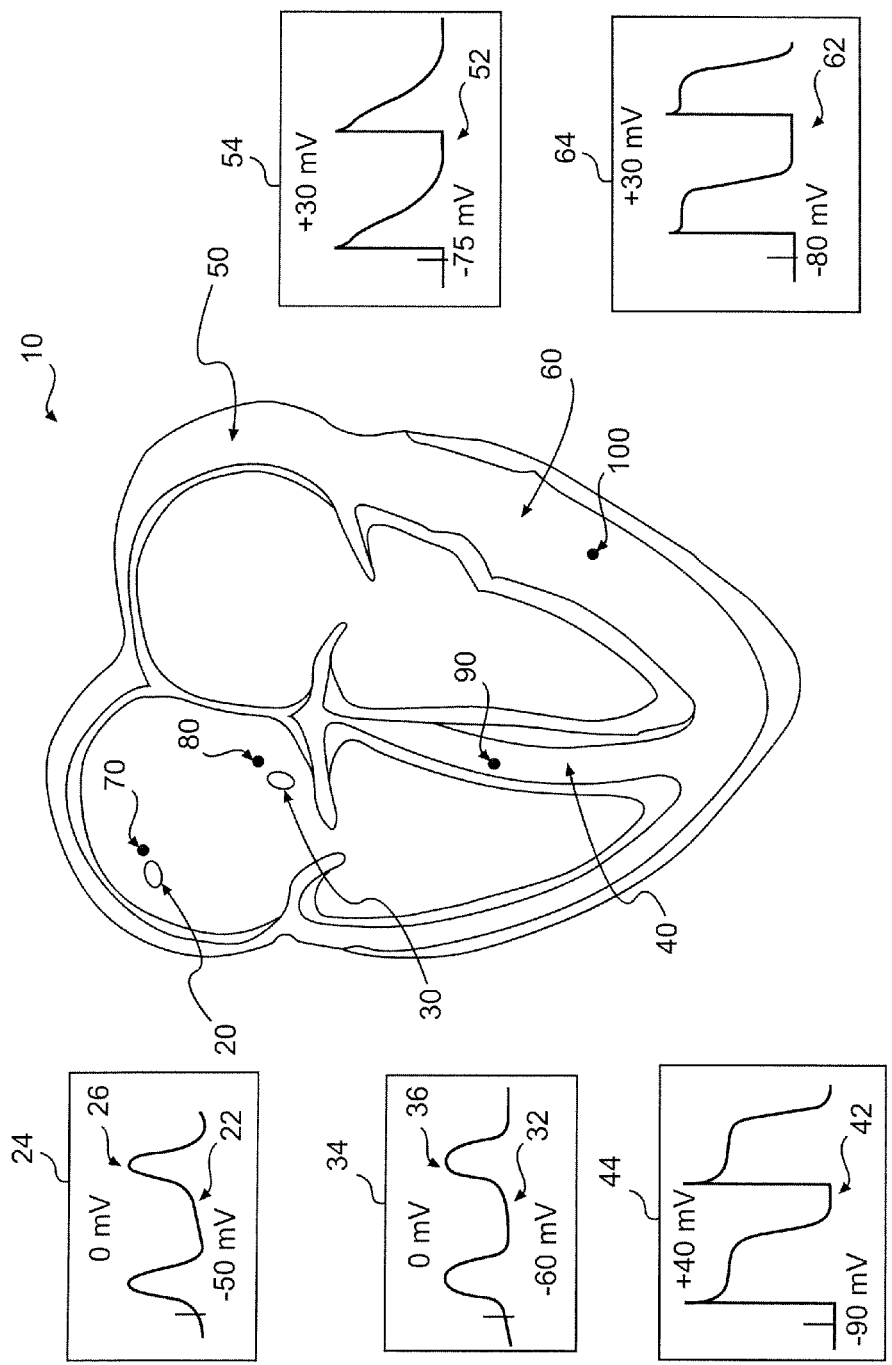
FIG. 1 illustrates a heart including action potentials associated with cells from various regions of the heart.

FIG. 1 illustrates a heart 10 and shows typical action potential (AP) waveforms from different heart regions. In a healthy heart a sino-atrial (SA) node 20 generates an AP 24 that propagates along various conduction pathways to other regions of the heart. Typically, AP 24 generated by SA node 20 travels through the right atrium to an atrio-ventricular (AV) node 30. From AV node 30, the AP travels out along conduction pathways to other heart regions, including the His-Purkinje fibers 40, the left atrium 50, and the left ventricle 60, leading to a coordinated contraction of the different heart chambers and efficient blood ejection.

APs observed from different regions of the heart often have different morphologies to AP 24 generated by SA node 20. As shown in FIG. 1, cells of AV node 30 typically generate an AP 34, while cells of His-Purkinje fibers 40 typically generate an AP 44. Cells of left atrium 50 and left ventricle 60 typically generate an AP 54 and an AP 64 respectively. The different morphologies of AP waveforms from different heart regions are in large part due to differences in expression and localization of ion channels in cells from the different heart regions. Ion channels may govern various ion fluxes, wherein ion channels may undergo conformational changes to permit or inhibit ion movement across a cell membrane. Ion channels may also be regulated by various physiological mechanisms, such as, for example, magnitude or rate of change of ion concentrations.

While cells of SA node 20 may typically generate an AP peak 26 about 70-80 times/minute, isolated cells of AV node 30 may typically generate an AP peak 36 about 40-60 times/minute. The difference in frequency of AP generation between cells of SA node 20 and AV node 30 is predominantly due to different rates of depolarization during the resting phase (diastole) of either cell type. Specifically, depolarization of cells of SA node 20 during resting phase 22 occurs at a faster rate than depolarization of cells of AV node 30 during resting phase 32. In contrast, APs from cells of His-Purkinje 40, atrium 50, and ventricle 60 show little or no diastolic depolarization, as indicated by the relatively flat regions of the respective AP resting phases shown by 42, 52, and 62.

Ion channels may function to form ion gradients across a cell membrane, wherein different ion concentrations are formed on different sides of the cell membrane. An ion gradient may also be described as a transmembrane potential ($V_m$), wherein a difference in voltage exists across a cell's plasma membrane. As $V_m$ changes, various ion channels may undergo conformational shifts due to local changes in ionic concentration. These conformational changes may in turn affect ion channel gating, leading to further opening and/or closing of various ion channels. Various molecular and biochemical aspects of cardiac ion channels are described in Schram et al., "Differential Distribution of Cardiac Ion Channel Expression as a Basis for Regional Specialization in Electrical function" Circulation Research vol. 90: p. 939-950 (2002); Satoh, Hiroyasu, "Sino-Atrial Nodal Cells of Mammalian Hearts: Ionic Currents and Gene Expression of Pacemaker Ionic Channels" J. Smooth Muscle Res. vol. 39(5): p. 175-193 (2003); and Kaupp et al., "Molecular Diversity of Pacemaker Ion Channels" Annu. Rev. Physiol. vol. 63: p. 235-257 (2001), all of which are hereby incorporated by reference in their entirety.

Diastolic depolarization 22 observed in cells of SA node 20 can also be described as a decrease in potential across a cell membrane. An important ion current associated with diastolic depolarization is termed "funny" current ($I_f$). This current is believed to be primarily responsible for the resting phase depolarization 22 observed in cells of SA node 20. $I_f$ is believed to arise predominantly from the non-specific movement of cations through HCN (hyper-polarization-activated and cyclic-nucleotide-gated) channels located in the cell membrane. Currently, four HCN isoforms are known and display high homology, but different voltage dependence, activation/deactivation kinetics, cyclic nucleotide modulation, and ion selectivity. The four HCN isoforms are also differently expressed throughout different heart regions, with the HCN4 variant showing highest expression in SA node 20 in humans.

Other channels and subunits are known to be preferentially expressed in SA node 20. For example, MiRP1, minK, $Ca_v3.1$-3.3, and Cx43 have been found to be more highly expressed in SA node 20 relative to other heart regions. These proteins and/or other channels, receptors, or other proteins expressed in cells of SA node 20 may at least partially contribute to the morphology and/or variability of AP 24. In addition, other proteins may be preferentially expressed in cardiomyocytes other than SA node 20. These proteins may at least partially contribute to the differences observed in AP morphology and/or variability in cells from different heart regions. For example, Kir2.1 has been shown to have greater expression in cells of left ventricle 60 and left atrium 50 relative to cells of SA node 20. Therefore reduced expression of one or more ion channels or other proteins in cells of SA node 20 relative to protein expression levels in cells of other heart regions may also contribute to differences in AP 24 relative to APs of other heart regions.

Diastolic depolarization mainly occurs through movement of ions across the cell membrane, in particular, fluxes of potassium, sodium, or calcium ions. The movement of these ions is highly dependent upon various ion channels and the regulation of such channels. Specific ion fluxes may further contribute to depolarization 22 and eventually lead to generation of AP peak 26. Such cellular activation may be affected by various compounds known to modulate pacemaker activity. For example, Isoprenaline is known to accelerate diastolic depolarization, leading to an increased frequency of AP generation, and thus increasing heart rate. In contrast, acetylcholine is known to slow diastolic depolarization, leading to a longer period between generation of consecutive APs, and thus decreasing heart rate. Such chemical regulation of heart rate occurs by affecting ion channel functionality, causing a population of ion channels to open and/or close at different voltages. Opening a channel at a lower voltage may permit increased ion flow and thus accelerate diastolic depolarization, while delaying the opening of a channel may decrease ion flow and thus slow diastolic depolarization.

An aspect of the present invention pertains to modulating heart rate via similar modulation of diastolic depolarization using systems, devices and methods to apply a local field stimulation (LFS), wherein the LFS is sub-threshold and alters a transmembrane potential of a pacemaker cell. Transmembrane potential, and therefore ion channel function, may be altered by an locally applied electric field. Changes in the applied field may modify activation, deactivation and/or functionality of various ion channels in the cell membrane. Such modification of ion channel functionality can modify the rate of spontaneous depolarization, and hence modulate heart rate.

Biological Pacemakers

Conventional implantable pacemakers are configured to electrically stimulate cardiac tissue to arrest conduction disturbances and/or initiate firing of APs of native tissue. In contrast, biological pacemakers (BPs) may include one or more cells of homogenous or heterogeneous type that can include native cells and/or be implanted in or around the heart. In some embodiments, a BP may include a cell colony wherein one or more cells of the cell colony may at least partially replicate a function and/or property of native pacemaker cells. The cell colony may include implanted cells and/or native cells, as described in detail below. For example, a cell colony may include at least one cell type configured to display similar electrophysiological functionality to cells of SA node 20 or AV node 30. Various aspects of biological pacemakers are described in Rosen et al, "Genes, stem cells, and biological pacemaker," Cardiovascular Research vol. 64: 12-23 (2004); Gepstein, Lior, "Stem cells as biological pacemakers," Expert Opin. Biol. Ther. vol. 5(12): 1531-1536 (2005); and U.S. Patent Publication 2004/0254134 to Marban et al., all of which are hereby incorporated by reference in their entirety.

In some embodiments, one or more BPs may be implanted at one or more of cardiac locations as shown in FIG. 1. In particular, BPs may be implanted at any suitable tissue location wherein the one or more BPs may affect cardiac function. BPs may be implanted within the atria, ventricles, interventricular septum, coronary sinus or other cardiac vasculature. Some patients may require a right atrial biological pacemaker 70 to at least partially replace a function of SA node 20. Other patients may require a BP 80 located near AV node 30. In addition, a BP 90 located within the interventricular septum may be effective for patients suffering conduction disturbances in His-Purkinje fibers 40. For such patients, the BP may be implanted at any location within the septum, including for example, near AV node 30 or more inferiorly near the cardiac apex. Further, a right ventricular BP (not shown) or a left ventricular BP 100 may be implanted at any suitable ventricular location.

BP Source

BPs may be derived from various tissue or cell sources, such as, for example, endogenous or exogenous cell sources, autologous, allogeneic, or xenogeneic sources. In particular, a BP may include at least one cell derived from an autograft, an isograft, an allograft, or a xenograft. In some embodiments, BPs may be derived from specific cell types or sources, such as, for example, cardiac myoblasts, skeletal myoblasts, stem cells or any other cellular source that may be treated, conditioned, or engineered to produce cells exhibiting suitable cellular functionality. For example, a myocardial cell source may include a sino-atrial node, an atrial-ventricular node, a His-Purkinje fiber, an atrium, or a ventricle. Different cell sources and types may offer specific advantages. For example, certain types of stem cells may exhibit greater ability to form functional gap junctions between cardiac myocytes and may reduce the likelihood of initiating arrhythmias.

Stem cells may include cells from various sources, and at various stages of differentiation. For example, BPs may be produced from pluripotent cell lines, which may be treated and/or genetically altered to produce desired electrophysiological properties. Stem cells may also include peripheral blood stem cells, bone-marrow derived stem cells, embryonic stem cells, and adult mesenchymal stem cells. Stem cells may be categorized by potency, which specifies the potential of the stem cell to form a specific cell type. Totipotent stem cells are produced from the fusion of an egg and sperm cell, and include cells produced by the first few divisions of the fertilized egg cell. These cells can grow into any type of cell without exception. Pluripotent stem cells are the descendants of totipotent cells and can grow into any cell type except for totipotent stem cells. Multipotent stem cells can produce only cells of a closely related family of cells (e.g. blood cells such as red blood cells, white blood cells and platelets). Unipotent cells can produce only one cell type, but have the property of self-renewal which distinguishes them from non-stem cells.

Stem cells may also be categorized according to their source, as either adult, embryonic or cord blood stem cells. Adult stem cells are undifferentiated cells found among differentiated cells of a specific tissue and are mostly multipotent cells, and have often been used in treatments of various diseases and conditions. Embryonic stem cells are cultured cells obtained from the undifferentiated inner mass cells of an early stage human embryo, while cord blood stem cells are derived from the blood of the placenta and umbilical cord after birth.

BP Modifications

Cells selected as BPs may be treated prior, during, or following tissue implantation. In particular, treatment may enhance one or more cellular functions and/or encourage differentiation into cardiomyocytes or cardiomyocyte-like cells having desired biological properties. For example, stem cells may be treated ex-vivo to encourage differentiation into appropriate cardiomyocyte cell types. Pre-implantation, selected cells may be combined with other materials to facilitate implantation, enhance engraftment, or promote cell viability pre- and/or post-implantation. For example, cells may be combined with culture media, extracellular matrix materials, pharmaceuticals, agents selected to control gene expression, antibiotics, and/or any other suitable material, as described in detail below. Following implantation, cells may be treated with electrical stimulation, as described by co-assigned U.S. Patent Publication 2004/0158290 to Girouard et al., which is hereby incorporated by reference in entirety. Post-implantation treatment may encourage gap junction formation between an implanted cell and adjacent myocyte.

Cells selected for use as BPs may be purified, treated, conditioned, or genetically engineered to produce desired properties. For example, cells may be configured to express genes associated with desired electrophysiological properties, as described in Rosen et al, "Genes, stem cells, and biological pacemaker," Cardiovascular Research vol. 64: 12-23 (2004). Such genes may include various ion channels selected to contribute to AP formation and/or propagation. Other genes may be selected to facilitate gap junction formation between adjacent cells and contribute to electrophysiological coupling between a BP and surrounding myocardium. Further, genes may be selected to provide desired responses to metabolic or hormonal changes, or to pharmaceuticals. In addition, genes may be selected to enhance cell viability, enhance BP engraftment post-implantation, control expression of other genes, promote angiogenesis, or alter local cellular functioning, as described in detail below.

A number of gene therapies have been developed that may be employed to convert one or more cells into a BP. For example, numerous transfection techniques may be used in vivo and/or in vitro to deliver genetic material to a suitable cell. Various genetic constructs encoding ion channels, gap functions, antagonists, and/or any other elements may be engineered and delivered to cells in order to at least partially provide pacemaker functionality. For example, cells may be extracted from a patient, purified, cultured and transfected in vitro, then implanted within cardiac syncytium. Some therapeutic strategies are described in Gepstein et al, "Somatic gene and cell therapy strategies for the treatment of cardiac arrhythmias," Am. J. Physiol. Heart Circ. Physiol. vol. 286: H815-H822 (2004) and Feld et al, "Electrophysiological modulation of cardiomyocytic tissue by transfected fibroblasts expressing potassium channels," Circulation vol. 105: 522-529, both of which are hereby incorporated by reference in their entirety. Following implantation, genetic expression may be controlled as described by co-assigned U.S. Patent Publication 2005/0192637 to Girouard et al., which is hereby incorporated by reference in entirety.

Various protocols may be used to form a BP exhibiting one or more cellular characteristics of SA node 20. For example, a protocol may include modifying the expression of one or more genes known to influence $V_m$, $I_f$, AP formation and/or propagation, transmembrane ion fluxes and/or other electrophysiological characteristics of SA node 20. In some embodiments, cells may be modified to express genes encoding receptors for circulating neuro-humoral factors, such as, for example, beta-adrenergic receptors. Increased expression of beta-adrenergic receptors may result in increased cellular signaling due to increased binding of circulating factors, leading to an increased AP generation. Other genes whose expression may be regulated include genes encoding ion channels, such as, for example, Kir2.1, HCN isoforms, calcium, potassium or sodium channels. In particular, regulating expression of one or more genes may reduce an outward hyperpolarizing current and/or increase an inward depolarizing current to accelerate diastolic depolarization, and thus increase AP generation. Further, the opposite strategy may be applied to delay diastolic depolarization to decrease AP generation and heart rate.

Numerous techniques are available to genetically modify cells, whereby a genetic construct may be incorporated in a cell. A genetic construct may include one or more partial sequences of any protein, peptide, transcription factor, RNA sequence, or any suitable nucleotide sequence. The genetic construct may at least partially encode an ion channel, a transcription factor, a membrane associated protein, a gap junction protein, a growth factor, a receptor, a cell development element, an apoptosis regulator, an antagonist, or an agonist. Also, the construct may include various regulatory sequences, markers (e.g. GFP), and may multiple open reading frames configured for co-expression. It is also contemplated that a genetic construct may include any modified genetic sequence, such as, for example, a sequence encoding an ion-channel modified using site-directed mutagenesis. Such a modified sequence may affect protein expression, processing, and/or functionality.

In some embodiments, genes encoding various pacemaker ion channels may be selected, as described in Satoh, Hiroyasu, "Sino-Atrial Nodal Cells of Mammalian Hearts: Ionic Currents and Gene Expression of Pacemaker Ionic Channels" J. Smooth Muscle Res. vol. 39(5): p. 175-193 (2003) and Kaupp et al., "Molecular Diversity of Pacemaker Ion Channels" Annu. Rev. Physiol. vol. 63: p. 235-257 (2001). Specifically, an ion channel may include HCN1, HCN2, HCN3, HCN4, Kir2.1, Kir3.1, Kir3.4, EGR, MiRP1, KvLQT1, minK, Kv4.2, Kv4.3, Kv1.4, KChIP2, Kv1.5, Kv3.1, Cav1.2, Cav1.3, Cav3.1, Cav3.2, Cav3.3, Nav1.5, a calcium channel, a sodium channel, a potassium channel, or combinations or isoforms thereof. Further, a gap junction protein may include connexin 40, connexin 43, connexin 45, or combinations or isoforms thereof. A growth factor may include vascular endothelial growth factor, fibroblast growth factor, transforming growth factor beta, transforming growth factor alpha, insulin-like growth factor, placental growth factor, hepatocyte growth factor, estrogen, follistatin, proliferin, prostaglandin E1, prostaglandin E2, cytokine, tumor necrosis factor, erythropoietin, granulocyte colony-stimulating factor, granulocyte macrophage colony-stimulating factor, angiogenin, platelet-derived growth factor, or combinations or isoforms thereof. In addition, a receptor may include a beta-adrenergic receptor, a cholinergic receptor, or combinations or isoforms thereof. An antagonist and/or an agonist may include peptide able to enhance or attenuate protein function, such as, for example, an antibody, an epitope, etc. In some embodiments the genetic construct may encode proteins, peptides or other elements that may alter or affect a cell's transmembrane potential or electrophysiological activity. Other factors may bind one or more ion channels to affect ion influx or efflux. Exemplary genes are described in Schram et al., "Differential Distribution of Cardiac Ion Channel Expression as a Basis for Regional Specialization in Electrical function" Circulation Research vol. 90: p. 939-950 (2002) and Rosen et al, "Genes, stem cells, and biological pacemaker," Cardiovascular Research vol. 64: 12-23 (2004).

Figure 2A:
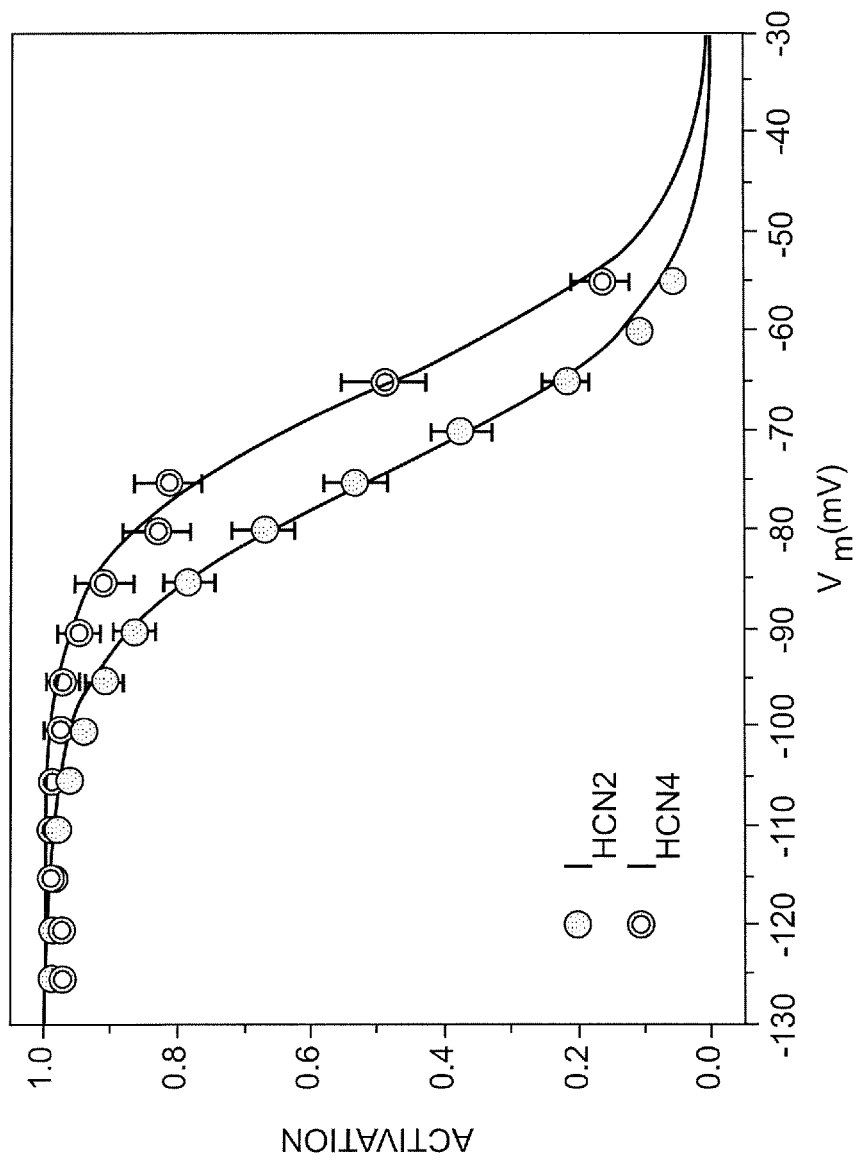
FIG. 2A illustrates activation curves for cells with modified HCN4 and HCN2 expression.

By way of an exemplary embodiment, FIG. 2A shows activation-voltage relations of ventricular cardiomyocytes expressing HCN2 and HCN4, as described in PCT application WO 02/098286 "Implantation of Biological Pacemaker That is Molecularly Determined", by Rosen et al. In general, the activation curves show a sigmoidal relationship with a cell's transmembrane potential $V_m$, whereby low absolute magnitude $V_m$ results in little or no activation of HCN2 or HCN4, and hence little or no $I_f$ flow across the plasma membrane. Conversely, at high absolute magnitude $V_m$, both HCN2 and HCN4 show almost complete activation, leading to enhanced $I_f$ flux across a cell's plasma membrane.

As previously described, a rate of diastolic depolarization may be generally dependent upon $I_f$, whereby ion movement across a plasma membrane may slowly depolarize the plasma membrane and consequently reduce the absolute magnitude of a cell's transmembrane potential $V_m$ (see diastolic depolarization 22, 32 as shown in FIG. 1). $I_f$ may be influenced by the type and/or distribution of ion channels within the plasma membrane and cells expressing various types and/or levels of ion channels may exhibit activation-voltage relationships different to that shown in FIG. 2A. For example, different ion channels may display different kinetics, rates of activation in relation to $V_m$, or result in different maximum action potentials. Hence a cell may be configured to display any number of activation-voltage relations such that $V_m$ may influence an ion flow across a cell's plasma membrane.

A cell's activation-voltage relation may be influenced by the application of an external field. For example, an externally applied field may elicit an action potential, as shown in Fromherz et al., "Silicon-Neuron Junction: Capacitive Stimulation of an Individual Neuron on a Silicon Chip" Physical Review Letters, vol. 75: p. 1670-1673 (1995), which is hereby incorporated by reference in entirety. Also, small changes in $V_m$ may result from an externally applied field, as shown in Sambelashvili et al., "Nonlinear effects in subthreshold virtual electrode polarization" Am. J. Physiol. Heart Circ. Physiol. vol. 284: H2368-H2374 (2003), which is hereby incorporated by reference in entirety. In some embodiments it may be possible to apply a field to a cell to cause the cell's $V_m$ to hyperpolarize or depolarize at least a few millivolts. For example, as shown in FIG. 2A, a shift of 2-5 mV on a steep part of a curve may result in a significant change in activation of HCN2 and/or HCN4. This increase or decrease in activation of these or other ion channels may affect various ion fluxes across a plasma membrane, such as, for example, $I_f$. Therefore, changing a field strength applied to a pacemaker cell may alter a rate of phase 4 depolarization, and hence modulate heart rate.

Figure 2B:
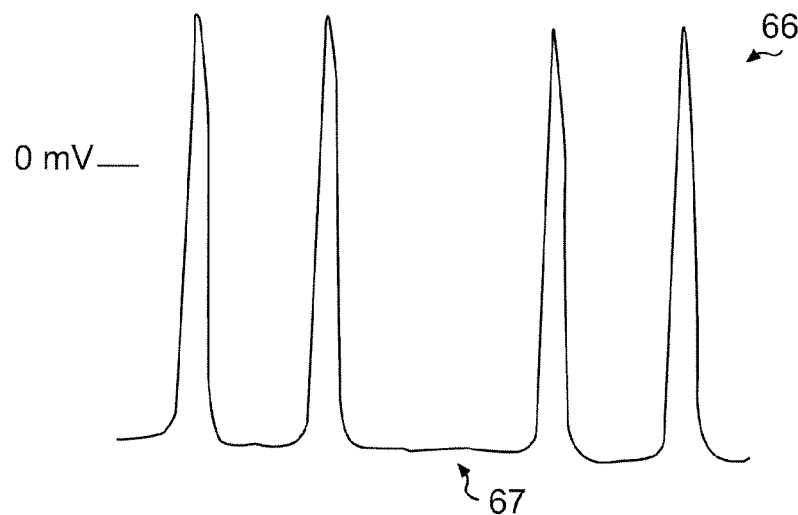
FIG. 2B illustrates an action potential for ventricular myocytes.
Figure 2C:
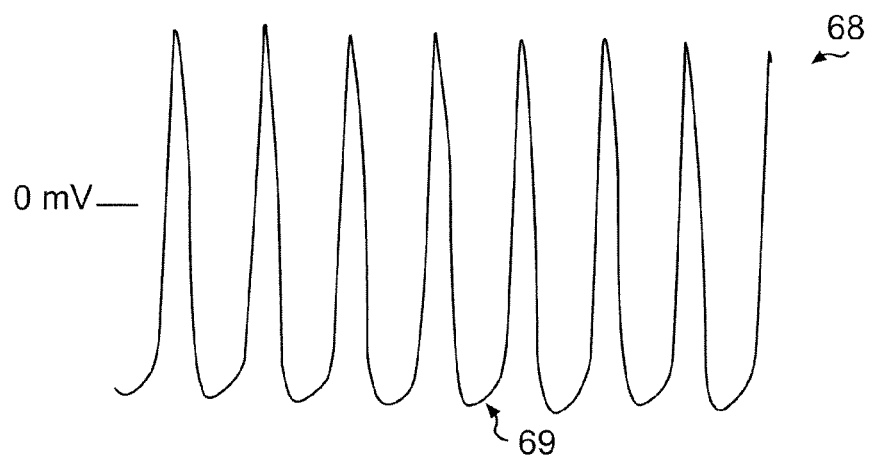
FIG. 2C illustrates an action potential for ventricular myocytes expressing HCN2.

FIGS. 2B and 2C show action potentials elicited from native ventricular cells and ventricular cells over-expressing HCN2 respectively, as described in PCT application WO 02/098286 "Implantation of Biological Pacemaker That is Molecularly Determined", by Rosen et al. While an AP waveform 66 from native ventricular cells shows little or no diastolic depolarization 67, an AP waveform 68 from HCN2 expressing ventricular myocytes show a slow diastolic depolarization 69. Over-expression of HCN2 may convert a cell displaying almost no diastolic depolarization (similar to ventricular AP 64 in FIG. 1), into cells displaying diastolic depolarization 69 (similar to diastolic depolarization 22 shown in AP waveform 24 for SA node 20 in FIG. 1). Therefore increasing $I_f$ during diastolic depolarization may lead to a faster and/or less variable rate of AP generation than observed in myocytes not expressing HCN2.

In some embodiments, a rate of AP generation from a cell may be altered by modulating expression of one or more genetic constructs of the cell. In particular, AP generation may be regulated by regulating levels of ion channel expression, or expressing one or more various ion channels, such as, for example, HCN2 and HCN4. FIG. 2A shows that cardiomyocytes expressing HCN4 may shift an activation-voltage curve more positive than HCN2-expressing cardiomyocytes. These data suggest that HCN4-expressing cells activate at less negative transmembrane voltages than HCN2-expressing cells. Thus HCN4-expressing cardiac cells may exhibit an increased rate of diastolic depolarization due to increased activation of HCN4 at less negative transmembrane voltages $V_m$. Such an increased rate of depolarization of HCN4-expressing cells may increase the rate of AP generation, and therefore increase heart rate. It is contemplated that any suitable number and/or type of cardiac cell may be modified to activate various ion channels at more negative voltages, whereby the rate of AP generation may be decrease. Such a cell type may offer the possibility of designing biological pacemakers to increase and/or decrease heart rate.

Traditional Pacemaker

Figure 3:
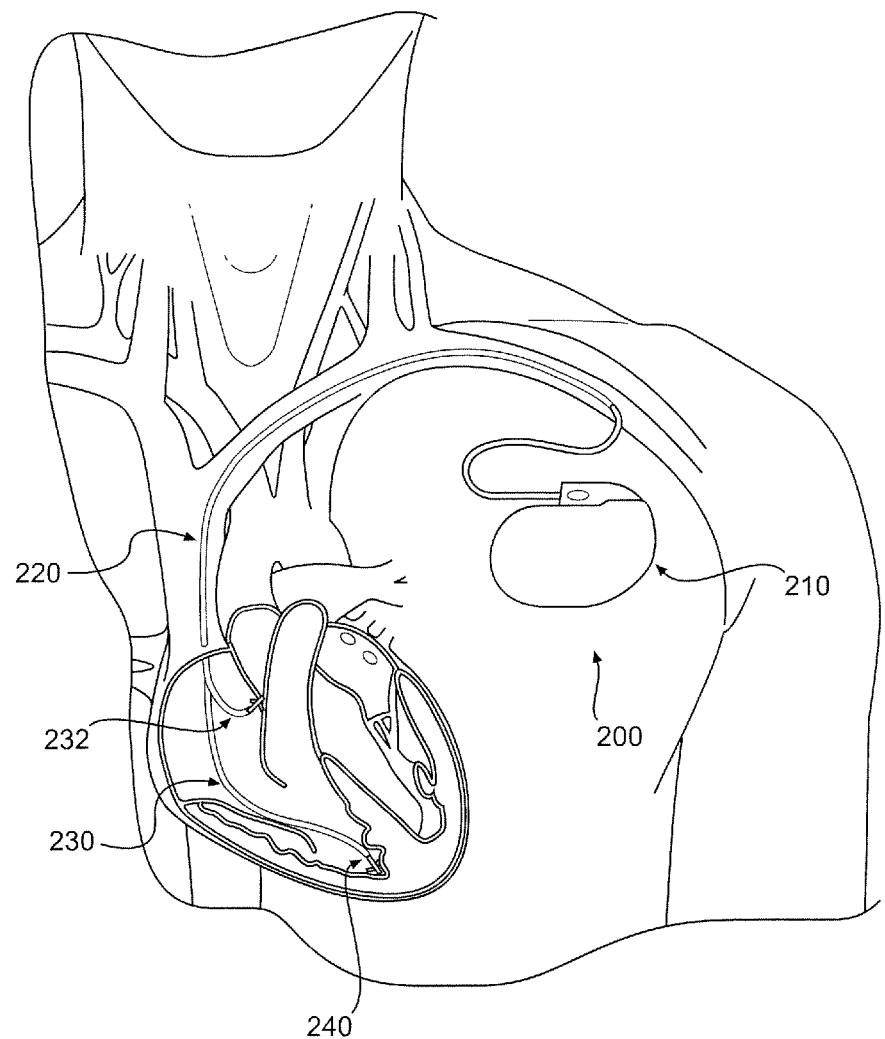
FIG. 3 illustrates a pacemaker implanted in a patient, according to an exemplary disclosed embodiment.

FIG. 3 illustrates an exemplary embodiment of a traditional dual-chamber pacemaker 200 that may be implanted to provide therapy for various cardiac indications. In some embodiments, pacemaker 200 includes a pulse generator 210 connected to a lead 220 fed into the heart through the superior vena cava. As shown, lead 220 may be bifurcated wherein lead 220 may split into a first one or more electrodes or lead 230 configured to stimulate the right ventricle, and a second one or more electrodes or lead 232 configured to stimulate the right atrium. As shown, two right-heart leads 230, 232 are provided, however any suitable number of leads may be selected and configured to stimulate contractile tissue. For example, one or more left heart electrodes or leads may also be provided through one or more coronary veins.

Different lead configurations may be selected based on a stimulation site, stimulation magnitude, and/or therapeutic application. For example, lead 220 may be configured for intra-myocardial, epicardial, endocardial, or intravascular placement. Lead 220 may also be configured to provide a stimulation of any suitable magnitude, such as a defibrillation stimulation where a high energy shock often requires delivery through a large surface area to reduce current density.

In some embodiments, lead 220 may include a coil and/or a cable. The coil or cable may include any suitable conductive material configured to conduct a signal. In addition, the coil may include any suitable configuration, such as, for example, a coaxial configuration or a coradial configuration.

Lead 220 may include one or more electrodes 240. As shown in FIG. 3, first lead 230 includes electrode 240. Electrode 240 may include any device configured to conduct a signal from lead 220 to target tissue to be stimulated. Electrode 240 may include any suitable electrode type, such as, for example, monopolar electrode, a bipolar electrode, or a multipolar electrode. Further, electrode 240 may include a defibrillation electrode, patch electrode, electrode array, or any electrode configuration known in the art. Electrode 240 may also include any suitable material, surface modification, and/or coating, as described in detail below.

Pacemaker 200 may be configured to monitor one of more physiological parameters, such as, for example, an ECG waveform component, a heart rate, a blood pressure, a blood gas level, or any suitable parameter known in the art. Pacemaker 200 may include one or more systems or devices configured to monitor one or more physiological parameters, such as, for example, an electrode, a pressure sensor, or a gas sensor. In some embodiments, lead 220 may include various electrodes and/or sensors configured to monitor a physiological parameter.

Pacemaker 200 may be configured to provide any pacing and/or defibrillation therapy known in the art. For example, any desired pacing mode (e.g. VDD, AAI, DDDR) or therapy (e.g. cardiac resynchronization therapy, post-MI therapies, and/or angiogenic stimulation) may be selected based on patient-specific characteristics. In particular, pacemaker 200 may also include any device or system configured to provide cardioversion or defibrillation shocks if required. It is also contemplated that pacemaker 200 may be configured to provide therapy via neuronal stimulation. For example, pacemaker 200 may be configured to provide stimulation to a patient's vagus nerve wherein lead 220 and/or electrode 240 may be configured to stimulate one or more vagus nerves. Such stimulation may be used to regulate heart rate and/or any other physiological parameter.

Local Field Stimulation (LFS)

An aspect of the present invention pertains to systems, devices and methods for providing a local field stimulation (LFS) to alter a cellular transmembrane potential $(V_m)$. Modulation of a cell's $V_m$ may affect one or more cellular functions, such as, for example, a movement of ions across the cell membrane. In some embodiments, modification of a cell's $V_m$ may affect a function of one or more proteins, such as, for example, ion channels. Modification of a cell's $V_m$ may cause a change in protein conformation and/or charge of one or more side-chains, thereby affecting protein functionality such that an ion flux across the cell's membrane may be altered, as shown in FIG. 2A. It is also contemplated that $V_m$ may affect a cellular function via other mechanisms.

As previously described and shown in FIGS. 2B and 2C, cardiac cells may exhibit an increased rate of AP generation due to altered expression levels of select ion channels. For example, an activation-voltage curve may be shifted due to varied gene expression, whereby a funny current may flow at transmembrane potentials of lesser absolute magnitude. Increasing and/or decreasing $I_f$ may function to increase and/or decrease a rate of diastolic depolarization of pacemaker-like cells, providing a mechanism to modulate a heart rate.

A similar effect may also be achieved via application of a LFS signal to a cell, wherein application of the LFS signal may alter an activation-voltage curve of the cell. Specifically, the LFS signal may modulate a cell's transmembrane potential, $V_m$, which may affect a function of one or more ion channels. Ion channel functionality may affect a rate of diastolic depolarization, and hence a rate of AP generation. Therefore, LFS may function to modulate a heart rate via modulation of a pacemaker cell's transmembrane potential. Further, such a stimulation may be subthreshold as the stimulation may not generate an AP, but rather alter a rate of AP generation through modulation of $V_m$.

LFS may include a subthreshold stimulation wherein the subthreshold stimulation may not be sufficient in magnitude and/or duration to depolarize a cell such that an AP is generated. Whereas traditional cardiac stimulation devices generally applied suprathreshold stimulations to depolarize a "critical mass" of myocardial cells, LFS may include lower energy stimulation that does not immediately depolarize the cells. Rather, LFS may provide a subthreshold stimulation that alters conditions or manipulates a cell's $V_m$ without causing immediate depolarization. Application of LFS may affect a cell's $V_m$ to modify a rate of AP generation by increasing or decreasing depolarization, however the strength of the LFS may not be sufficient to cause an all-or-nothing depolarization. Any LFS signal should be sufficient to affect $V_m$ such that a heat rate may be modified.

LFS may be applied locally, wherein LFS may stimulate a local population of cells. Local stimulation may be necessary as the influence of LFS may not extend beyond a local cellular region. For example, LFS may be applied to a cellular region of cardiac tissue of less than 10 mm in diameter. In some embodiments, an LFS stimulation device may be in contact with one or more cells such that LFS may be applied to the one or more cells.

The local affect of LFS may be dependent upon a virtual electrode effect, whereby cellular stimulation may create virtual electrodes due to asymmetric conduction properties of cardiac tissue. Tissue anisotropy is thought to account for the virtual electrode effect, as discussed in Knisely et al., "Virtual Electrode Effects in Myocardial Fibers" Biophysical Journal vol. 66: 719-28 (1994), which is hereby incorporated by reference. More recent work has shown similar results using subthreshold stimulation, as described in Akar et al., "Optical measurement of cell-to-cell coupling in intact heart using subthreshold electrical stimulation" Am. J. Physiol. Heart Circ. Physiol. vol. 281: H533-H542 (2001), which is hereby incorporated by reference.

As described previously, LFS is not intended to generate an AP. Rather, LFS may affect a function of one or more ion channels, wherein altering a membrane potential may alter ion flow across the membrane without generating an AP (see FIG. 2A). Application of an LFS signal may not immediately generate an AP, but may affect functioning of ion channels associated with AP generation and/or other cellular activation mechanisms. In contrast to LFS, a traditional suprathreshold stimulation usually generates an AP immediately following application of a cathodal signal or immediately following cessation of an anodal signal.

A traditional stimulation signal (e.g. a pacing or defibrillation pulse) directly depolarizes the cell to a threshold level such that the intrinsic ion channel activity may generates an AP. Conversely, LFS may be applied to regulate a cell's transmembrane potential for approximately the duration of the applied LFS signal. Whereas traditional stimulation sought to exceed a cell's threshold stimulation, LFS may be more precisely delivered to apply a lower energy that may influence the cell's native electrophysiological activity, rather than interrupt or reset such activity as does traditional therapy. For example, LFS may be applied to pacemaker cells to regulate a heart rate via modulation of a rate of depolarization during diastole. LFS may be applied to alter $V_m$ to increase a rate of diastolic depolarization to increase a rate of AP generation, and hence increase heart rate. Alternatively, LFS may be applied to alter $V_m$ to decrease a rate of diastolic depolarization to decrease a rate of AP generation, and hence decrease heart rate.

LFS may include any suitable stimulation waveform. In particular, LFS may include a cathodal waveform component, an anodal waveform component, a sequential or overlapping biphasic waveform component, or combinations thereof. LFS may also include any suitable subthreshold energy, such as, for example, a current density of 0.1-10 $mA/mm^2$. Further, an LFS may be applied periodically or continuously. It is also contemplated that the timing of a LFS may be dependent upon a suitable physiological parameter, such as, for example, an ECG waveform component, such as, a P-wave, an T-wave, a QRS complex, or an S-T interval. LFS may also be employed for rate regulation in rate-responsive pacing, in response to physiologic demand.

LFS may affect various cellular functions via modulation of a cell's $V_m$. In some embodiments, LFS may affect a cell's response to circulating factors, local contraction or expansion forces, or local electrophysiological activity. For example, LFS may modulate a conduction parameter of a cell, wherein a conduction parameter may include any parameter associated with the generation or conduction of an electrophysiological signal. In particular, a conduction parameter may include a frequency of AP generation, an AP waveform component, or a conduction velocity. The LFS signal may be modulated using any suitable method, such as, for example, a feed-back mechanism, a look-up table, or other system.

In some embodiments, LFS may be applied to any suitable type of tissue within a local region. As previously described, LFS may be applied to a localized cell population due to attenuation of an LFS signal within the stimulated tissue region. Tissue suitable for LFS may include cardiac, neuronal, gastric, or any other tissue type whereby LFS may modulate a cell's $V_m$ to affect one or more cellular functions. For example, LFS applied to cardiac tissue may affect a cellular, localized or organ-wide conduction and/or contraction disturbance. In particular, LFS may be applied to modulate a heart rate and/or treat a cardiac condition, such as, node dysfunction, atrioventricular conduction disturbance, heart failure, or arrhythmia. Node dysfunction may include any condition abnormality associated with an SA node or AV node, such as, for example, sick sinus syndrome, SA block, sinus tachycardia, AV block, or similar condition.

LFS may be applied to alter at least one cell's $V_m$. Specifically, LFS may alter a function of one or more cells of a cell colony wherein a cell colony includes one or more cells of similar type. LFS stimulation of a cell colony may alter a $V_m$ of one or more cells of the cell colony such that a cellular function of the cell colony may be modified. LFS may also be applied to a plurality of cell colonies alternatively and/or simultaneously.

A cell colony may include one or more cardiomyocytes from SA node 20, AV node 30, or His-Purkinje fibers 40. Also, cells of similar type may include cells displaying similar function, cells from a common source, cells expressing one or more similar proteins, or cells containing similar genetic constructs. A cell colony may include heterogeneous cell types, and/or cells at different stages of development. In some embodiments, a cell colony may include one or more cells of native tissue and/or a biological pacemaker.

In some embodiments, a LFS may be applied to BP 70 wherein the LFS may alter a $V_m$ of one or more cells of BP 70. Modulating a $V_m$ of one or more cells of BP 70 may affect one or more cellular functions of BP 70, such as, for example, a rate of depolarization during diastole. Specifically, increasing a rate of depolarization during AP resting phase 22 of one or more of BP 70 may increase a rate of AP generation. Further, LFS may be applied to produce the opposite effect wherein the rate of AP generation from SA node-like cells is decreased. In particular, a rate of depolarization during diastolic depolarization may be decreased, thereby decreasing a rate of AP generation. Therefore, LFS applied to SA node 20, SA node-like cells, and/or BP 70 may increase or decrease AP generation from the stimulated cells, leading in turn to an increase or decrease in heart rate.

The devices, systems and methods of the present disclosure may permit modulation of cellular functionality through the application of LFS to a cell colony, wherein the LFS may be subthreshold and may alter a $V_m$ of one or more cells of the cell colony. In some embodiments, the devices, systems and/or methods of the present disclosure may be used to modulate a cell colony located in the cardiac region, such as, for example, one or more BPs. For example, the rate of AP generation from a BP may be increased or decreased through alteration of $V_m$ of one or more cells of the BP. In other embodiments, the devices, systems and/or methods of the present disclosure may be adapted for use in non-cardiac tissue, such as, for example, neuronal, gastric or intestinal tissue. For example, LFS may be applied to control sphincter contraction or relaxation, nerve conduction, or promote or impede gastric motility.

In some embodiments, LFS may be applied using an existing pacemaker 200, such as shown in FIG. 3. Pacemaker 200 may be modified wherein pulse generator 210 may include hardware and/or software configured to provide LFS. For example, pacemaker 200 may include one or more leads 220 and/or electrode 240 configured to provide LFS. In addition, pacemaker 200 may be configured to provide LFS to one or more BPs. In particular, pacemaker 200 may be configured to provide LFS to native tissue and/or one or more BPs when required, such as, for example, when native tissue is not functioning correctly, or a BP is not providing sufficient function.

In some embodiments, pacemaker 200 may be configured to provide non-LFS pacing therapy immediately following implantation of the BP. Such stimulation may be required until the BP has become engrafted and functions properly. In other embodiments, pacemaker 200 may be configured to continuously or periodically evaluate the performance of one or more BPs and provide non-LFS pacing therapy (e.g. DDD-R) if the BP is determined to be functioning improperly. Such a method is disclosed by co-assigned U.S. patent application Ser. No. 11/745,667, "System and Method for Determining the Origin of a Sensed Beat," which is hereby incorporated by reference. Pacemaker 200 may also include one or more leads 220 configured to provide a signal to one or more electrodes 240, wherein electrodes 240 may be configured to provide LFS to one or more BPs. Various other components of pacemaker 200 may be similarly modified as described below.

LFS System

In some embodiments, a pulse generator and lead separate from pacemaker 200 may be configured to provide LFS. For example, an independent system may be configured to provide LFS to one or more BPs. It is also contemplated that the independent system may include one or more components external to a patient's body.

Figure 4:
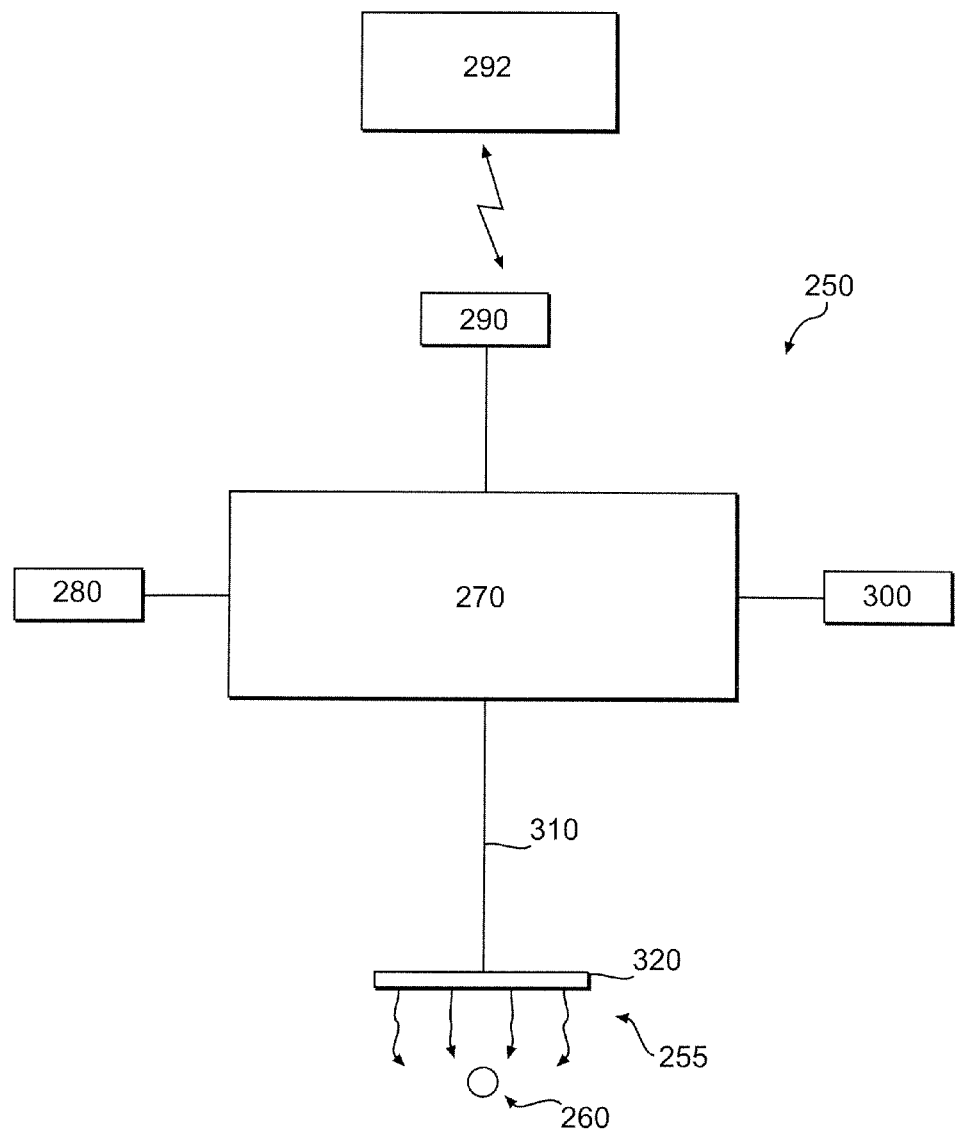
FIG. 4 illustrates a local field stimulation system, according to an exemplary disclosed embodiment.

FIG. 4 shows a block diagram representing a LFS system 250 for providing a LFS signal 255 to one or more cells of a cell colony 260. In some embodiments, LFS system 250 may stimulate cell colony 260, wherein cell colony 260 may include one or more BPs. In particular, cell colony 260 may include BP 70 wherein one or more cells of cell colony 260 may include SA node-like cells. For example, cell colony 260 may include one or more stems cells configured to express HCN2, HCN4, or combinations thereof.

LFS system 250 may include a microprocessor 270, a memory 280, a telemetry system 290, an energy source 300, a lead 310, and an electrode 320. Microprocessor 270 may be configured to control application of LFS signal 255, wherein energy stored in energy source 300 may be transmitted via lead 310 to electrode 320. Further, microprocessor 270 may retrieve information from memory 280 to control the application and/or timing LFS. In some embodiments, LFS system 250 may be reprogrammable whereby a remote device 292 may be configured to transmit one or more signals to telemetry system 290 to provide or modify information stored within memory 280. LFS system 250 may apply LFS signal 255 to one or more cells of cell colony 260 via electrode 320, wherein LFS signal 255 may modulate a $V_m$ of one or more cells of cell colony 260. In some embodiments, one or more components of LFS system 250 may be degradable.

LFS system 250 may be modified and/or include additional components configured to permit microprocessor 270 to monitor one or more physiological parameters. A physiological parameter may include a cardiac waveform component, a heart rate, a blood pressure, a blood constituent, pH, cardiac output, a blood flow, a heart wall movement, an activity or posture state, a respiration state, a conduction velocity, or an action potential. In some embodiments, LFS system 250 may include one or more leads 310 and/or electrodes 320 configured to monitor a physiological parameter. Microprocessor 270 may be any suitable processor configured to provide tissue stimulation, and may include hardware and/or software configured to monitor any suitable physiological parameter. In addition, microprocessor 270 may be configured to control application of LFS signal 255 to one or more cell colonies 260, wherein LFS may be applied periodically, continuously, or timed to coincide with a suitable physiological parameter, such as, for example, a cardiac waveform component.

Memory 280 may include any suitable hardware configured to store data, such as, for example, data representing an LFS stimulation regime. Memory 280 may include a random access memory, a read only memory, a flash memory, an electrically erasable and programmable read only memory, an electrically programmable read only memory, or any suitable type of data storage device known in the art. Memory 280 may also be configured to store instructions, patient or hardware identification information, security information, and may be re-writable such that data may be modified, added or deleted.

Telemetry system 290 may be configured to communicate a signal between LFS system 250 and remote source 292.

Communicating a signal may include transmitting and/or receiving a signal from either LFS system 250 or remote source 292. Telemetry system 290 may include any hardware and/or software required to communicate a signal. For example, telemetry system 290 may include an antenna or similar device configured to communicate a signal to remote source 292. A signal may include any data that may be communicated between remote source 292 and LFS system 250, such as, for example, data representing an LFS stimulation regime, patient information, device data, etc. It is also contemplated that telemetry system 290 may be configured to transmit and/or receive energy. For example, telemetry system 290 may be configured to receive energy transmitted transcutaneously from a power source external to a patient. Also, telemetry system 290 may be configured to communicate with an implantable medical device (IMD, not shown) if LFS system 250 is separate from the IMD.

Energy source 300 may include any suitable device configured to store energy, and may be rechargeable. For example, energy source 300 may include a capacitor, a battery, or similar device. In some embodiments, energy source 300 may be provided by an implantable medical device, such as, for example, a pacemaker, a neurostimulator, a drug delivery device, or any other IMD known in the art. In some embodiments, energy source 300 may be rechargeable. Energy source 300 may be operably connected to microprocessor 270 and/or other components of LFS system 250 such that energy source 300 may provide power to various components of LFS system 250. In particular, energy source 300 may be configured to store energy required to apply LFS signal 255 to cell colony 260.

Lead 310 may be configured to conduct energy to electrode 320 such that LFS signal 255 may be applied to cell colony 260. Lead 310 may also be configured to connect to various connectors and/or headers, using standard or proprietary terminal designs. In addition, lead 310 may be any size, shape, of have any suitable mechanical or chemical property required to permit LFS. For example, lead 310 may be bifurcated, and may be operably connected to one or more electrodes. Lead 310 may be any configuration, such as any shape and/or size designed for intra-myocardial, epicardial, endocardial, or vascular placement. For example, lead 310 may include a helical configuration and be of suitable stiffness to maintain a position with a coronary sinus.

Lead 310 may include any suitable conductive material known in the art. In addition, lead 310 may include various coatings and be formed of various insulative materials, such as, for example, silicone, silastic, polyurethane, urethane, rubber, silicone rubber, polyethylene, and/or combinations thereof. Also, lead 310 may include one or more conductive coils and/or cables, and may include a coaxial and/or coradial configuration.

Electrode 320 may include any device configured to transmit LFS signal 255 to target tissue to be stimulated. In particular, electrode 320 may be configured to stimulate BP 70 with LFS signal 255 to alter diastolic depolarization. Electrode 320 may include any suitable electrode type, such as, for example, monopolar electrode, a bipolar electrode, or a multipolar electrode. Further, electrode 320 may include a defibrillation electrode, patch electrode, electrode array, or any electrode configuration known in the art. In some embodiments, electrode 320 may be configured for intra-myocardial placement, endocardial placement, epicardial placement, or vascular placement. Electrode 320 may also include any suitable material, surface modification, and/or coating. For example, electrode 320 may include platinum, titanium, gold, stainless steel, iridium and alloys and combinations thereof. Further, electrode 320 may include any appropriate anchoring system and/or may be adapted for drug delivery, as described in detail below.

In some embodiments, a component of lead 310 and/or electrode 320 may be degradable. Specifically, one or more regions of lead 310 and/or electrode 320 may include a material designed to degrade within some time period, such as, for example, a day, a week, a month, a year, or several years. In particular, a component may be configured to degrade due to biological, chemical or electrical mechanisms. Further, electrode 320 and/or lead 310 may be at least partially coated, wherein a coating may include a polymer, a ceramic, an alloy, or a therapeutic agent. In addition, lead 310 and/or electrode 320 may include a partially modified surface. For example, a modified surface may include various surface treatments that may enhance tissue stimulation, prolong device life, reduce immune response, or other suitable process known in the art.

Electrode 320 and/or lead 310 may further include an anchoring system (not shown) configured to at least partially maintain a position of a device relative to tissue to be stimulated. For example, an anchoring system may include a passive or an active system. A passive system may include a tine, a plate, or a similar element configured to resist movement following placement of a device into the tissue. An active system may include a retractable system, such as, for example, a screw. In some embodiments, an anchoring system may be degradable.

Electrode 320 may be configured to provide LFS to one or more cells of cell colony 260, wherein LFS signal 255 may modulate a $V_m$ of one or more cells of cell colony 260. However, LFS may only operate over a limited range, such as, for example, less than 10 mm as previously described. In some embodiments, electrode 320 may be configured to provide LFS over a limited distance, such as, for example, 10 mm.

Electrode Configurations

Figure 5:
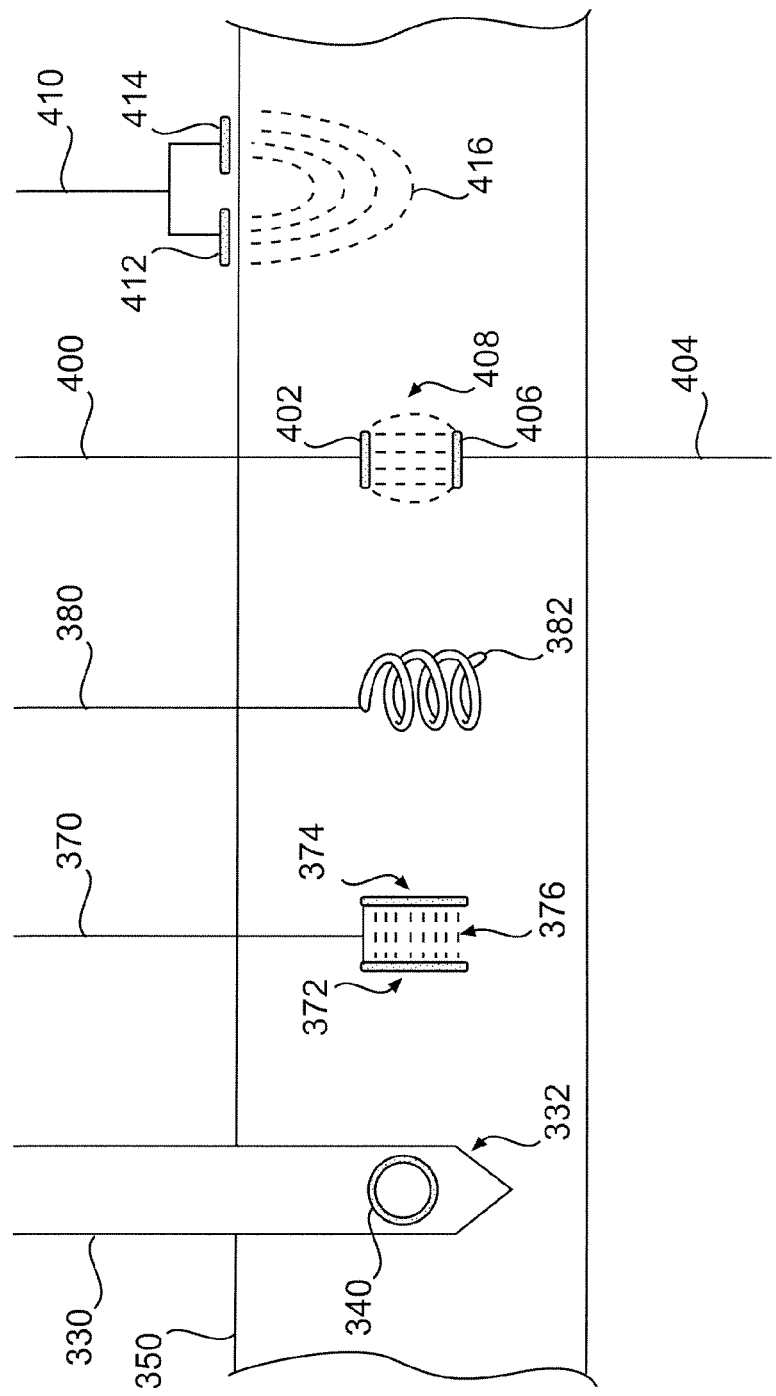
FIG. 5 illustrates several electrode configurations, according to several exemplary disclosed embodiments.

FIG. 5 illustrates various electrode configurations, according to several exemplary disclosed embodiments. For example, a lead 330 may include a circular electrode 340, wherein electrode 340 may be configured to apply a uniform LFS to cells located adjacent to electrode 340. In some embodiments, electrode 340 may be monopolar, bipolar, or multipolar. Lead 330 may also include a sharpened distal end 332 configured to aid insertion into a target tissue, such as, for example, a heart wall 350. Lead 330 may also include various anchoring systems (not shown), such as, for example, tines, screws or other passive or active anchoring devices known in the art.

In another exemplary embodiment, lead 370 may include two electrodes 372, 374 configured to provide a LFS signal 376 in a direction parallel to heart wall 350. It is also contemplated that electrodes may be configured to provide LFS at any orientation relative heart wall 350 or striated cardiac myocytes. For example, two electrodes may be configured within heart wall 350 to provide LFS in a direction perpendicular to heart wall 350.

In another exemplary embodiment, a lead 380 may include a helical electrode 382. As shown, helical electrode 382 may be positioned within heart wall 350 and may be located by rotating helical electrode 382 relative to heart wall 350. Helical electrode 382 may permit anchoring of helical electrode 382 within tissue to maintain a position of electrode 382 relative to heart wall 350. Further, helical electrode 382 may also be configured for vascular placement, wherein the helical structure may be dimensioned to provide a fit within a vessel to maintain a position of helical electrode 382 within the vessel. Such a vessel-located electrode may be configured to provide LFS into a specific tissue region adjacent to the vessel. In some embodiments, a lead (not shown) may be include a helical conformation dimensioned to maintain a position of the lead within a vessel via frictional forces.

In another exemplary embodiment, an endocardium lead 400 may be connected to an endocardial electrode 402 and an epicardium lead 404 may be connected to an epicardial electrode 406. Endocardial electrode 402 and epicardial electrode 406 may be configured to provide opposite poles of a LFS signal 408, such that the myocardium located between electrodes 402, 406 is stimulated by LFS.

In another exemplary embodiment, a bifurcated lead 410 may include two surface electrodes 412 and 414. Electrodes 412 and 414 may be positioned to form a LFS signal 416 that may extend into heart wall 350 sufficient to alter $V_m$ of one or more cells within heart wall 350. Further, lead 410 and/or electrodes 412, 414 may include an anchoring system (not shown) configured to maintain the position of electrodes 412, 414.

LFS System Embodiments

It is also contemplated that LFS system 250 may include additional or fewer components than listed. For example, in some embodiments LFS system 250 may not require energy source 300 if telemetry system 290 is configured to receive energy remotely, as described below. Also, LFS system 250 may include a plurality of leads 310 to stimulate a plurality of cell colonies 260. Further, LFS system 250 may be configured to monitor heart rate, BP function, pacing rate, AP propagation, and/or components of an ECG waveform.

Various components of LFS system 250 may be configured to operate independently or in conjunction with pacemaker 200. As previously discussed, LFS system 250 may be integrated with an existing implantable pacemaker 200, wherein lead 310 may be connected to pulse generator 210. In other embodiments, one or more components of LFS system 250 may be configured to operate in conjunction with pacemaker 200. In still other embodiments, LFS system 250 may operate as an independent or stand-alone system. The design and/or configuration of LFS system 250 may depend on a particular treatment required, such as, for example, expected duration of stimulation regime, timing of stimulation regime, battery size, patient age, etc.

LFS system 250 may be configured based on various factors, including estimated duration of stimulation, energy of stimulation, location of BP, etc. For example, an anticipated duration of LFS application may affect the size of energy source 300. In particular, if LFS system 250 is configured to operate for days, weeks or years, the size of energy source 300 will likely vary to accommodate the different energy storage capacities. For example, LFS system 250 may be configured to provide stimulation for several days to several weeks, and may thus require a relatively small energy source 300. In some embodiments energy source 300 may be rechargeable.

In some embodiments, LFS system 250 may be configured to be incorporated into a capsule (not shown), that may be implanted directly into the myocardium. Such a capsule system may not require lead 310 as electrode 320 may be located on a surface of the capsule. In some embodiments, the capsule system may not require memory 280 and/or energy source 300 as functionality of these components may be provided by remote source 292 configured to transmit power and/or data to telemetry system 290. Further, remote source 292 may be located in pulse generator 210 or external to a patient. Remote device 292 located externally may be configured to transmit power and/or data signals to the capsule system, wherein the capsule system may receive the signals via telemetry system 290 and provide LFS to cell colony 260 via one or more electrodes 320. It is also contemplated that a plurality of capsule systems may be provided at various locations throughout a heart to provide LFS to a plurality of BPs. Such a capsule LFS system may provide an acute stimulation regime wherein long-term LFS of a BP is not required.

As discussed above, LFS system 250 may include a leadless system whereby lead 310 may not be required. LFS system 250 may include various devices and/or systems configured to transmit and/or receive signals wirelessly. For example, LFS system 250 may include one or more "planet" systems containing microprocessor 270 and other components configured to transmit one or more signals to control LFS application to one or more cell colonies 260. The "planet" system may communicate with one or more "satellite" systems that may include electrode 320 configured to apply LFS to one or more cell colonies 260. Such a planet/satellite system may permit LFS application to one or more BPs. Further, the planet system may be located external to the patient's heart, such as, for example, in a blood vessel whereby the planet system may include a stent configuration. It is also contemplated that the planet system may be located in another position within a patient's body or may be located external to a patient's body. An advantage of such a planet/satellite system may include reduced tissue trauma associated with placement of the planet and/or satellite systems due to reduced system size.

Cell Colony Preparation

Local field stimulation may provide a method to modulate a function of a cell colony by affecting a transmembrane potential of one or more cells of the cell colony. As previously described, LFS may only be effective over a limited range, such as, 10 mm. Therefore, a stimulation device should be placed within sufficient proximity to the cell colony for application of a LFS signal to the cell colony following implantation. However, positioning a stimulation device within close proximity to an implanted cell colony may prove difficult using currently available medical technology. A more suitable solution may include growing a cell colony in vitro in or on devices and/or systems configured to permit application of LFS to the cell colony following implantation. For example, a system may be configured to permit growth of a cell colony on, or within close proximity to, electrodes configured to apply LFS. Such a system may permit growth of a cell colony and further not require separate implantation and/or positioning of the cell colony and stimulation device. The system may also be configured such that less manipulation of the cell colony is required prior to implantation, which may enhance post-implantation cellular viability.

Implantation of a cell colony may cause significant cell loss, damage and/or stress to implanted cells, that may affect the long term survival and/or function of the cell colony. Further, trauma to native tissue associated with an implantation procedure may cause inflammatory or other responses at the implantation site, further affecting the long term survival and/or function of the cell colony. For example, the implanted cells may not establish sufficient molecular connections with native tissue, leading to insufficient formation of gap junctions or other connections necessary to ensure adequate electrophysiological functioning of the implanted cells. Therefore systems, devices and/or methods may be required to minimize adverse effects of a cell colony implantation procedure.

In some embodiments, one or more cells of a cell colony may be grown in vitro prior to implantation. For example, one or more cells may be grown in vitro prior to transplantation into a patient's heart wherein the cells may be configured to function as a BP. Specifically, a cell colony may be configured to function as a BP to supplement and/or replace a patient's SA node.

As previously described, various technologies exist to create cells suitable for use as a cell colony. For example, one method of forming suitable cells may include extracting one or more cells from a patient, growing and/or purifying cells in vitro, which may or may not include genetically altering the cells, and then implanting the cells into the patient. It is also contemplated that select cell lines may be developed for general use as cell colonies for multiple patients.

In some embodiments, a cell cassette 420 may be configured to reduce cell loss, damage and/or stress associated with implantation of a cell colony. FIG. 6A shows cell cassette 420, wherein cell cassette 420 may include a cell medium 425 configured to receive one or more cells of a cell colony (not shown) prior to implantation of the cell colony in a target tissue. Cell medium 425 may include any material able to maintain cellular viability. For example, cell medium 425 may include a salt, a buffer, a cell nutrient, a factor, or any other compound required by a cell to maintain viability. Cell medium 425 may also include any suitable cellular scaffold, such as, for example, a mixture of extracellular proteins, a hydrogel, a polymer matrix, a plastic, a ceramic, or a metal alloy. The cellular scaffold may include any structure or surface configured to permit cellular adhesion, such as, for example, a porous surface, a bead, or a gel. Further, cell medium 425 may be configured to reduce cell migration, or may include factors to aid cell recovery, reduce an immune response, or promote transcription.

In some embodiments, a component of cell cassette 420 may be degradable. For example, cell cassette 420 may include a outer shell (not shown) including a biodegradable material. The outer shell may be configured to protect a cell colony during an implantation procedure and degrade following the implantation procedure. One or more degradable components of cell cassette 420 may permit a cell colony additional time to adapt to different environment.

Cell cassette 420 may also be configured to permit application of LFS to the cell colony following implantation of the cell colony. For example, cell cassette 420 may be dimensioned for placement within a stimulation device configured to transmit an LFS signal to one or more cells of an implanted cell colony. As previously described, a stimulation device should be located within 10 mm of any implanted cells to ensure sufficient modulation of $V_m$ of the implanted cells. Therefore, cell cassette 420 may be dimensioned for placement within a stimulation device such that the stimulation device may be located within 10 mm of an implanted cell colony.

Cell cassette 420 and/or the stimulation device should be configured to reduce any adverse effects of any in vitro procedures. For example, cell cassette 420 and/or the stimulation device should be configured to permit rapid insertion of cell cassette 420 in the stimulation device while causing minimal damage to a cell colony.

Figure 7A:
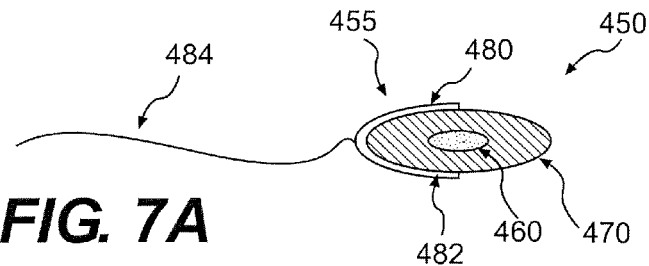
FIG. 7A illustrates a cell cassette, according to an exemplary disclosed embodiment.
Figure 7B:
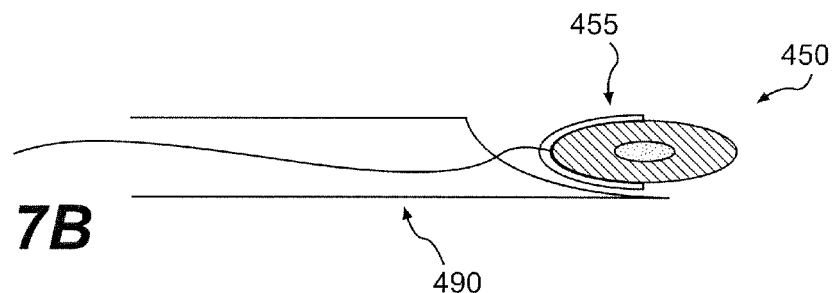
FIG. 7B illustrates a cell cassette and an insertion device, according to an exemplary disclosed embodiment.

In some embodiments, cell cassette 420 may include one or more electrodes configured to generate an LFS signal, as described below and shown in FIG. 7A-7C. Cell cassette 420 may also be configured for placement over an electrode. For example, cell cassette 420 may include a hollow tube sealed at one end and configured for placement over an electrode wire. Cell cassette 420 may be suspended in cell media such that one or more cells may adhere to the outer surface of cell cassette 420. Following adequate cell growth, cell cassette 420 may be slid over the electrode wire and implanted.

Cell cassette 420 may also be configured to permit alignment of cells of cell colony with a stimulation device. As described in detail below, cells of cell colony may be grown in a substantially similar orientation. To enhance AP generation and/or propagation, it may be advantageous to align a stimulation device such that a field of LFS is generally orientated relative to an orientation of a cell colony. For example, a LFS applied perpendicular to a longitudinal axis of a SA node like cell may enhance AP generation.

In some embodiment, cell cassette 420 may be configured to operate with a pre-implantation system 427. FIG. 6B shows pre-implantation system 427, wherein pre-implantation system 427 may include a receptacle 428 configured to receive cell cassette 420. The one or more cells of a cell colony that may be placed in cell cassette 420 may originate from multiple sources, as described previously. For example, the cell colony may include one or more stem cells, wherein a stem cell may be isolated, grown, purified and/or cultured using any known or future developed techniques. In addition, a cell of the cell colony may be genetically altered as described above, using any suitable sequence, such as, for example, a HCN2 gene and/or a HCN4 gene.

Pre-implantation system 427 may be configured to maintain viability of one or more cells of a cell colony in vitro. Specifically, pre-implantation system 427 may be configured to provide an environment suitable to grow and/or sustain a cell colony. For example, pre-implantation system 427 may be configured to provide a cell colony with a salt, a buffer, a cell nutrient, a factor, an oxygen supply, or any other element or compound required by the cell to maintain viability. Further, pre-implantation system 427 may be configured to permit growth and/or differentiation of the cell colony. For example, pre-implantation system 427 may be configured to permit genetic alteration of a cell colony in vitro, such as, adding a HCN4 gene to one or more cells.

In some embodiments, pre-implantation system 427 may be configured to permit application of an electrical stimulation to a cell colony in cell cassette 420, wherein the electrical stimulation may include any suitable energy range and/or duration. It is also contemplated that pre-implantation system 427 may be configured to provide any suitable cell conditioning. For example, a cell colony may be conditioned in vitro with any suitable form of stimulation, such as, electrical, mechanical, chemical or other forms of stimulation. Such stimulation may pre-condition a cell colony before implantation and may train one or more cellular functions. It is also contemplated that such conditioning may be used to grow, maintain, and/or differentiate certain cell types.

In some embodiments, cell cassette 420 may be configured to store and/or ship a cell colony. For example, the cell colony may be grown or placed in cell medium 425 configured for shipment as cell cassette 420 may be produced at one location and shipped to another for implantation. It is also contemplated that cell cassette 420 may be frozen for ease of handling. Various factors may also be added to cell medium 425 to enhance the survivability of the cell colony. Future advances in cell production, storage and/or transport may be contemplated within the scope of this disclosure.

FIG. 6C shows a lead 430 configured to receive cell cassette 420. Lead 430 may be any suitable design as previously discussed, and may include a sharp distal tip 432 configured to aid implantation. Further, lead 430 may include one or more electrodes, such as, for example, a left electrode 434 and a right electrode 436. Cell cassette 420 may be configured for to permit LFS to the cell colony as described above. Specifically, cell cassette 420 may be configured for placement within lead 430 such that electrodes 434, 436 may be located within 10 mm of the cell colony contained within cell cassette 420.

FIG. 6D shows lead 430 containing cell cassette 420 implanted in tissue, such as, for example, a heart wall 440. Lead 430 may include an anchoring system (not shown), and may be operably connected to a pulse generator (not shown), as previously described. In some embodiments, the cell colony within cell cassette 420 and/or cell cassette 420 may be oriented with respect to lead 430 and/or heart wall 440. For example, cell cassette 420 may be positioned relative to heart wall 440 such the cell colony and striated cardiomyocytes are in a substantially similar orientation. It is contemplated that AP generation and/or propagation may be enhanced by specific orientation or placement of cell colony within heart wall 440. In particular, application of LFS to cells of the cell colony of a select orientation relative to native tissue may affect modulation of $V_m$ of implanted and/or native cells.

In some embodiments, a cell cassette 450 may be combined with a stimulation device, such as, for example, an electrode configured to apply LFS to a cell colony. FIG. 7A shows cell cassette 450 including a stimulation device 455. A cell colony 460 may be located within a cell medium 470 of cell cassette 450, wherein cell colony 460 and cell medium 470 may be any suitable cell type and medium as previously described. In addition, cell cassette 450 may be operably associated with stimulation device 455 such that stimulation device 455 may be configured to apply LFS to cell colony 460. In some embodiments, stimulation device 455 may include a top electrode 480, a bottom electrode 482, and/or a lead 484.

In some embodiments, cell cassette 450 may be formed prior to seeding one or more cells of cell colony 460 in cell medium 470. For example, cell medium 470 may be attached to stimulation device 455, forming cell cassette 450. Cell cassette 450 may then be seeded with one or more cells of cell colony 460 and placed in a pre-implantation system (not shown) as previously described. Cell colony 460 may remain viable, grow, develop, and/or differentiate following seeding. Such cellular processes may continue until transportation or implantation of cell cassette 450. Formation of cell colony 460 within cell cassette 450 may include formation of cell colony 460 within 10 mm of top electrode 480 and/or bottom electrode 482 such that an LFS signal may be applied to cell colony 460. Thus, cell cassette 450 may reduce cell damage or cell death that may result from any additional steps required to prepare cell colony 460 for implantation.

In some embodiments, cell cassette 450 may be configured to be implanted using a traditional needle or catheter. FIG. 7B shows cell cassette 450 configured and dimensioned to be placed within a needle 490 for positioning within tissue (not shown). As shown, cell cassette 450 may being positioned in a target tissue beyond a distal tip of needle 490. Various systems and/or devices may be used to insert and position cell cassette 450 in a desired location and/or desired orientation, as described below. It is also contemplated that cell cassette 450 may include an anchoring system (not shown) as previously described.

In some embodiments, stimulation device 455 may include lead 484 operably connected to a pulse generator (not shown). It is also contemplated that stimulation device 455 may include a self contained LFS system (not shown), wherein stimulation device 455 includes a microprocessor, battery and other components of LFS system as previously discussed. Such a system could be placed in a desired location in a single step and would generally not require placement of a pulse generator or lead attachment.

Figure 7C:
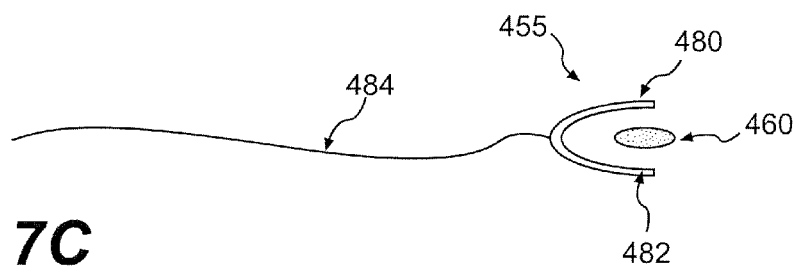
FIG. 7C illustrates a cell cassette post-implantation, according to an exemplary disclosed embodiment.

FIG. 7C shows cell cassette 450 post-implantation, wherein cell medium 470 has degraded. In some embodiments, cell medium 470 may be biodegradable. As shown in FIG. 7C, cell medium 470 may include one or more degradable components that may be configured to degrade under suitable biological conditions. It is further contemplated that other components of cell cassette 450 may be degradable. For example, electrodes 480, 482 may be configured to degrade after the useful life of electrodes 480, 482 has been reached. In addition, lead 484 may be configured to degrade within a time period or to facilitate an explant of one or more components of cell cassette 450. Degradable components may permit enhanced LFS of cell colony 460 and/or enhanced function of cell colony 460.

In some embodiments, degradation of cell medium 470 may release anti-inflammatory or other factors designed to reduce a biological immune response. In addition, the degradation of cell medium 470 may release various factors designed to enhance one or more functions of cell colony 460. The factors may also promote or hinder cell growth, division, migration, differentiation, and/or development. Further, cell cassette 450 may be configured to permit conditioning of cell colony 470 to adapt to a local environment or perform a desired function. In addition, cell cassette 450 may be configured to minimize scar tissue formation, immune response or other biological reactions associated with the implantation of cell colony 460.

Cell Colony Implantation

Implantation of a stimulation device and/or system configured to apply LFS to a cell colony posses several challenges. Initially, a site within a target tissue for cell colony implantation may require accurate determination. In some applications, inaccurate placement of a cell colony may lead to reduced functionality of the cell colony. Further, in order to stimulate an implanted cell colony, the stimulation device and/or system should be located within 10 mm of the cell colony. Current surgical techniques and technologies may not provide sufficient resolution to permit device and/or system placement within the tolerances required to apply LFS to a previously implanted cell colony. Therefore, the need exists for devices and/or systems configured to determine a tissue site for implantation of a cell colony with suitable precision, to deliver the cell colony to the target site with suitable precision, and deliver a stimulation device and/or system to the target tissue such that LFS may be applied to the implanted cell colony. Ideally, these steps should also be achieved with minimal local tissue trauma, or cell death or damage to the cell colony.

Figure 8A:
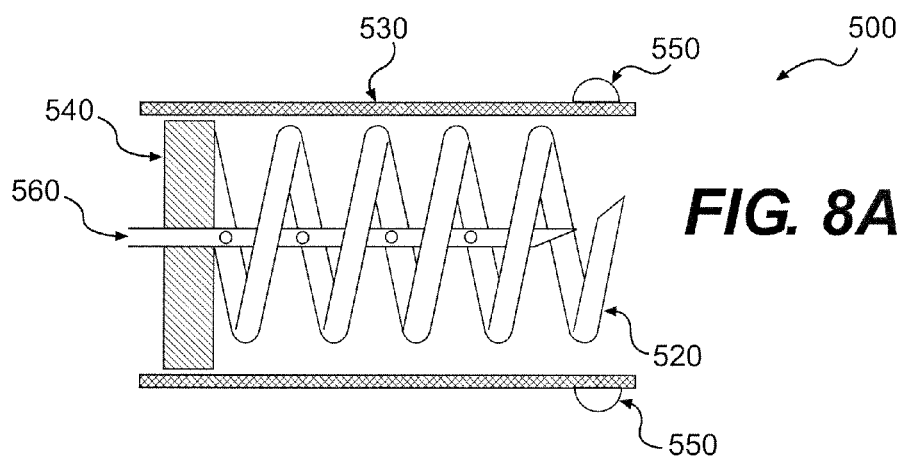
FIG. 8A illustrates an insertion device, according to an exemplary disclosed embodiment.

FIG. 8A shows an insertion device 500 according to an exemplary embodiment. Insertion device 500 may include any medical device configured to insert a cell colony 510 (see FIG. 8C) and a stimulation device 520 within a target tissue such that stimulation device 520 may apply LFS to cell colony 510. In some embodiments, stimulation device 520 may include one or more electrodes positioned within 10 mm of cell colony 510 (see FIG. 8C).

Insertion device 500 may include any medical device configured to position cell colony 510 and stimulation device 520 in close proximity in target tissue, such as, for example, within 10 mm. In some embodiments, insertion device 500 may include a needle, a catheter, a trocar, an obturator, a cannula, or similar hollow device. Insertion device 500 may also include a conduit 530 configured to permit insertion of cell colony 510 and/or stimulation device 520 in a target tissue. Insertion device 500 may further include a moveable member 540 configured to move cell colony 510 and/or stimulation device 520 relative to conduit 530 to permit implantation of cell colony 510 and/or stimulation device 520.

In some embodiments, cell colony 510 may require precise placement in a target tissue in order to properly function in vivo. For example, a BP implanted into cardiac tissue may require implantation in close proximity to a patient's native SA node. In addition, the direction of LFS relative to an implanted BP, and/or relative to native striated cardiac myocytes may affect BP functionality. Therefore, insertion device 500 may be configured to operate in conjunction with known positioning systems or be modified to utilize similar techniques.

Various techniques to determine a site of implantation of cell colony 510 within a target tissue may exist or may be developed in the future. For example, a site for implantation may be determined using a positioning system configured to operate using any suitable technique, such as, electrophysiological mapping, fluoroscopy, magnetic positioning, radio-opaque markers, positron-emission tomography, single-photon emission computed tomography, magnetic resonance imaging, chemical markers, cell imaging techniques, echo-planar imaging, or angiography. Implantation device 500 may be appropriately configured to operate with any suitable positioning system. For example, implantation device 500 may include one or more distal radio-opaque markers 550 configured to permit positioning using fluoroscopic techniques.

In some embodiments, a cell cassette (not shown) may include various positioning systems and/or be configured for precise implantation. Various implantation devices 500 may be configured to properly position the cell cassette within a target tissue. As shown in FIG. 7B, cell cassette 450 may be implanted using needle 490. Following precise placement of cell cassette 450, needle 490 may be removed with minimal disruption to the natural tissue. In some embodiments, a cell cassette may be configured for positioning using one or more techniques described above, such as, for example, radio-opaque markers.

Figure 8B:
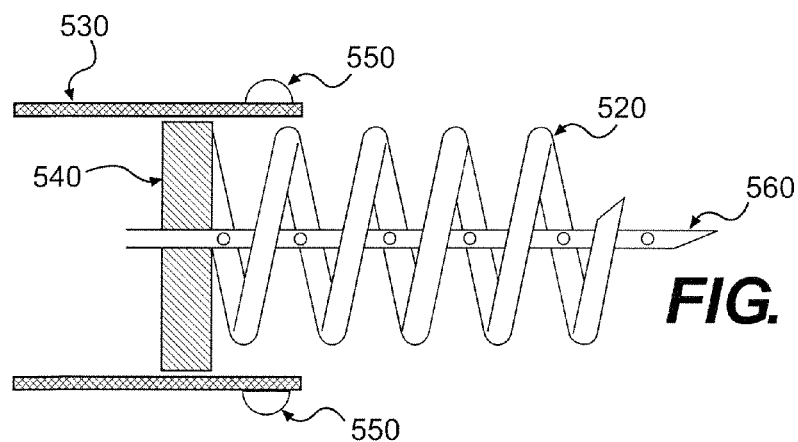
FIG. 8B illustrates an insertion device in an extended configuration, according to an exemplary disclosed embodiment.

FIG. 8B shows implantation device 500 with stimulation device 520 extending from the distal tip of implantation device 500. In some embodiments, stimulation device 520 may include a radio-opaque material such that a position of stimulation device 520 relative to distal radio-opaque markers 550 may be determined using fluoroscopy. Such a design embodiment may permit precise positioning of stimulation device 520 within a target tissue.

In some embodiments, a target tissue site of cell colony 510 may require treatment before, during, or after implantation of cell colony 510. For example, a local region of native tissue surrounding a location where cell colony 510 may be implanted may require pre-treatment with a factor to prepare a suitable environment for the engraftment of cell colony 510.

Implantation device 500 may include a delivery system 560. FIG. 8A shows delivery system 560 in a retracted position within implantation device 500. Delivery system 560 may be configured to deliver one or more therapeutic agents to a target tissue prior to, during, or following implantation of cell colony 510. Delivery system 560 may include an active agent-delivery system, a passive agent-delivery system, and/or any suitable agent-delivery system known in the art. For example, an agent-delivery system may include a mechanical pump (not shown), a coating (not shown), or any other appropriate device configured to deliver one or more therapeutic agents, such as, immunosuppressive, anti-inflammatory, or toxic factors. It is also contemplated that an agent-delivery system may be associated with an LFS system configured to permit slow-release of an agent following cell colony implantation.

In some embodiments, cell colony may benefit by injection of one or more factors prior to tissue implantation of the cell colony. For example, delivery system 560 may include a needle configured to deliver a therapeutic agent. The therapeutic agent may enhance survivability, attenuate an immune response, enhance expression, or modify a biological process. Such agents may include a small molecule, a nucleic-acid sequence, a peptide, a protein, a polymer, and/or any other suitable molecule. In particular, a therapeutic agent may include an ion channel, a transcription factor, a membrane associated protein, a gap junction protein, a growth factor, a cell survival factor, a receptor, a cell development factor, an apoptosis regulator, an antagonist, or an agonist. In addition, a therapeutic agent may include an anti-inflammatory agent, such as, for example, a corticosteroid to reduce irritation of tissue adjacent to an electrode.

FIG. 8B shows delivery system 560 in an extended position relative to implantation device 500. In particular, delivery system 560 may extend beyond a distal tip of implantation device 500 such that an agent may be applied to a target tissue. The agent may be applied to prepare a site for implantation of stimulation device 520 and/or cell colony 510.

Figure 8C:
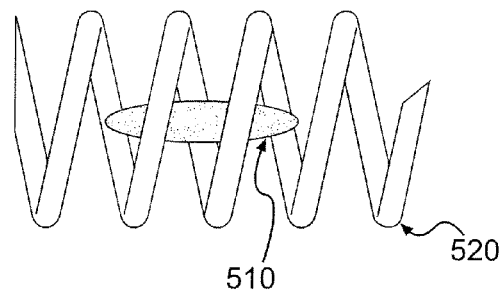
FIG. 8C illustrates an implanted cell colony and stimulation device, according to an exemplary disclosed embodiment.

FIG. 8C shows cell colony 510 and stimulation device 520. Specifically, stimulation device 520 may be located within 10 mm of cell colony 510 such that a LFS signal may be applied to cell colony 510. As shown, stimulation device 520 includes a helical electrode configuration. Rotating a helical electrode may reduce trauma to tissue adjacent to an implantation site, leading to reduced time for cell colony 510 to become functional. It is also contemplated that stimulation device 520 may include one or more electrodes in any suitable configuration as previously described.

In some embodiments, implantation device 500 may be configured to perform one or more additional functions prior to, during, or following implantation of cell colony 510. For example, cell colony 510 may be configured to function as a BP and may be implanted to replace a patient's SA node. As such, at least some cells of a native SA node may require treatment to at least partially inhibit their function prior to implantation to reduce the likelihood of arrhythmias generated by mis-functioning tissue. Also, the cell colony may operate more efficiently if the cell colony is implanted in close proximity to the site of the native SA node. Therefore, implantation device 500 may be configured to treat a target tissue prior to implantation of the cell colony, wherein treatment may include ablation, dosage with a toxic agent or other suitable treatment designed to reduce tissue function.

Preferred embodiments of the present invention have been described above. Those skilled in the art will understand, however, that changes and modifications may be made to these embodiments without departing from the true scope and spirit of the invention, which is defined by the claims.

What is claimed is:

1. A method of increasing a patient's heart rate, comprising:

increasing a rate of diastolic depolarization of a cell colony to increase the patient's heart rate without spontaneously depolarizing the cell colony by applying a first local field stimulation (LFS) signal to the cell colony, the cell colony formed in vitro and implanted within a cardiac tissue of the patient, wherein the cell colony comprises cardiomyocytes derived from stem cells and contains a genetic construct that encodes at least part of an ion channel, the genetic construct encoding at least one of HCN2 and HCN4, wherein the first LFS signal comprises a sub-threshold stimulation pulse and has a current density less than 10 mA/mm$^2$.

2. The method of claim 1, wherein the first LFS signal is applied continuously to the cell colony.

3. The method of claim 1, wherein the first LFS signal is applied uniformly to the cell colony.

4. The method of claim 1, wherein the first LFS signal alters transmembrane potentials of the cell colony located less than approximately 10 mm from a stimulation device applying the LFS signal to the cell colony.

5. The method of claim 1, wherein the cardiac tissue includes at least one of the sino-atrial node and the atrio-ventricular node.

6. A method of modulating a heart rate of a patient, comprising: providing a device configured to apply a local field stimulation (LFS) signal to a cell colony formed in vitro and implanted generally within at least one of the sino-atrial node and the atrio-ventricular node of the patient, wherein the cell colony comprises cardiomyocytes derived from stem cells and contains a nucleotide sequence that encodes at least one of HCN2 and HCN4; increasing the rate of diastolic depolarization by applying the LFS signal without spontaneously depolarizing the cell colony, wherein the LFS signal comprises a sub-threshold stimulation pulse and wherein the LFS signal modulates the patient's heart rate without interrupting or resetting the patient's heart rate.

7. The method of claim 6, wherein the sub-threshold stimulation pulse has a current density of less than 10 mA/mm$^2$.

* * * * *